(12) United States Patent
Colleran et al.

(10) Patent No.: US 7,867,251 B2
(45) Date of Patent: *Jan. 11, 2011

(54) REATTACHMENT OF TISSUE TO BASE TISSUE

(75) Inventors: Dennis Colleran, North Attleborough, MA (US); Stefan Gabriel, Mattapoisett, MA (US)

(73) Assignee: Smith & Nephew, Inc., Memphis, TN (US)

( * ) Notice: Subject to any disclaimer, the term of this patent is extended or adjusted under 35 U.S.C. 154(b) by 206 days.

This patent is subject to a terminal disclaimer.

(21) Appl. No.: 10/305,998

(22) Filed: Nov. 27, 2002

(65) Prior Publication Data

US 2003/0120309 A1    Jun. 26, 2003

Related U.S. Application Data

(63) Continuation-in-part of application No. 09/986,376, filed on Nov. 8, 2001, now Pat. No. 6,656,183.

(51) Int. Cl.
*A61B 17/04* (2006.01)
(52) U.S. Cl. ................................... 606/232
(58) Field of Classification Search ......... 606/232, 606/72, 73, 300, 301, 304, 309, 310, 327, 606/233
See application file for complete search history.

(56) References Cited

U.S. PATENT DOCUMENTS

| | | |
|---|---|---|
| 4,532,926 A | 8/1985 | O'Holla |
| 4,548,202 A | 10/1985 | Duncan |
| 4,632,100 A | 12/1986 | Somers et al. |
| 4,946,468 A | 8/1990 | Li |
| 5,002,550 A | 3/1991 | Li |
| 5,013,316 A | 5/1991 | Goble et al. |
| 5,037,422 A | 8/1991 | Hayhurst et al. |
| 5,041,129 A | 8/1991 | Hayhurst et al. |
| 5,100,417 A | 3/1992 | Cerier et al. |
| 5,123,913 A | 6/1992 | Wilk et al. |
| 5,152,790 A | 10/1992 | Rosenberg et al. |
| 5,156,616 A | 10/1992 | Meadows et al. |
| 5,192,303 A | 3/1993 | Gatturna et al. |
| 5,224,946 A | 7/1993 | Hayhurst et al. |
| 5,236,445 A | 8/1993 | Hayhurst et al. |
| 5,258,016 A | 11/1993 | DiPoto et al. |

(Continued)

FOREIGN PATENT DOCUMENTS

EP    0 464 480    1/1992

(Continued)

OTHER PUBLICATIONS

PCT International Search Report, May 4, 2004, 9 pages.

(Continued)

*Primary Examiner*—Thomas C Barrett
*Assistant Examiner*—Michael J Araj
(74) *Attorney, Agent, or Firm*—Fish & Richardson P.C.

(57) ABSTRACT

An anchor includes an anchor body configured to be retained within base tissue. The anchor body includes a unidirectional mechanism to selectively restrict passage of a flexible member through the anchor. The flexible member includes a loop to enable attachment of candidate tissue to base tissue without the use of knots.

44 Claims, 18 Drawing Sheets

U.S. PATENT DOCUMENTS

| | | |
|---|---|---|
| 5,261,914 A | 11/1993 | Warren |
| 5,282,809 A | 2/1994 | Kammerer et al. |
| 5,312,438 A | 5/1994 | Johnson |
| 5,324,308 A | 6/1994 | Pierce |
| 5,330,491 A | 7/1994 | Walker et al. |
| 5,336,240 A | 8/1994 | Metzler et al. |
| 5,354,298 A | 10/1994 | Lee et al. |
| 5,370,662 A | 12/1994 | Stone et al. |
| 5,372,604 A | 12/1994 | Trott |
| 5,383,905 A | 1/1995 | Golds et al. |
| 5,391,173 A | 2/1995 | Wilk |
| 5,403,348 A | 4/1995 | Bonutti |
| 5,411,523 A | 5/1995 | Goble |
| 5,417,691 A | 5/1995 | Hayhurst |
| 5,423,860 A | 6/1995 | Lizardi et al. |
| 5,464,427 A | 11/1995 | Curtis et al. |
| 5,472,452 A | 12/1995 | Trott |
| 5,480,403 A | 1/1996 | Lee et al. |
| 5,486,197 A | 1/1996 | Le et al. |
| 5,501,683 A | 3/1996 | Trott |
| 5,522,843 A * | 6/1996 | Zang ........................ 606/232 |
| 5,522,844 A | 6/1996 | Johnson |
| 5,522,846 A | 6/1996 | Bonutti |
| 5,534,011 A | 7/1996 | Greene, Jr. et al. |
| 5,536,273 A | 7/1996 | Lehrer |
| 5,545,180 A | 8/1996 | Le et al. |
| 5,554,171 A | 9/1996 | Gatturna et al. |
| 5,569,306 A | 10/1996 | Thal |
| 5,571,139 A | 11/1996 | Jenkins, Jr. |
| 5,573,548 A | 11/1996 | Nazre et al. |
| 5,578,057 A | 11/1996 | Wemstrom, Jr. |
| 5,584,835 A | 12/1996 | Greenfield |
| 5,584,860 A | 12/1996 | Goble et al. |
| 5,591,177 A | 1/1997 | Lehrer |
| 5,601,557 A | 2/1997 | Hayhurst |
| 5,605,457 A * | 2/1997 | Bailey et al. ............... 433/174 |
| 5,609,597 A | 3/1997 | Lehrer |
| 5,630,824 A | 5/1997 | Hart |
| 5,643,320 A | 7/1997 | Lower et al. |
| 5,645,589 A | 7/1997 | Li |
| 5,647,874 A | 7/1997 | Hayhurst |
| 5,658,313 A | 8/1997 | Thal |
| 5,665,112 A | 9/1997 | Thal |
| 5,669,935 A | 9/1997 | Rosenman et al. |
| 5,683,419 A | 11/1997 | Thal |
| 5,690,676 A | 11/1997 | DiPoto et al. |
| 5,702,397 A | 12/1997 | Goble et al. |
| 5,709,708 A * | 1/1998 | Thal ........................... 606/232 |
| 5,720,765 A | 2/1998 | Thal |
| 5,720,766 A | 2/1998 | Zang et al. |
| 5,725,529 A | 3/1998 | Nicholson et al. |
| 5,725,556 A | 3/1998 | Moser et al. |
| 5,725,557 A | 3/1998 | Gatturna et al. |
| 5,728,136 A | 3/1998 | Thal |
| 5,728,864 A | 3/1998 | Motoyama et al. |
| 5,733,307 A | 3/1998 | Dinsdale |
| 5,735,875 A | 4/1998 | Bonutti et al. |
| 5,741,300 A | 4/1998 | Li |
| 5,782,862 A | 7/1998 | Bonutti |
| 5,782,864 A | 7/1998 | Lizardi |
| 5,782,866 A | 7/1998 | Wenstrom, Jr. |
| 5,810,848 A | 9/1998 | Hayhurst |
| 5,810,854 A | 9/1998 | Beach |
| 5,814,051 A | 9/1998 | Wenstrom, Jr. |
| 5,824,011 A | 10/1998 | Stone et al. |
| 5,827,291 A | 10/1998 | Fucci et al. |
| 5,843,087 A | 12/1998 | Jensen et al. |
| 5,885,294 A | 3/1999 | Pedlick et al. |
| 5,891,168 A | 4/1999 | Thal |
| 5,893,592 A | 4/1999 | Schulze et al. |
| 5,897,564 A | 4/1999 | Schulze et al. |
| 5,897,574 A | 4/1999 | Bonutti |
| 5,899,920 A | 5/1999 | DeSatnick et al. |
| 5,904,696 A | 5/1999 | Rosenman |
| 5,906,624 A | 5/1999 | Wenstrom, Jr. |
| 5,911,721 A | 6/1999 | Nicholson et al. |
| RE36,289 E | 8/1999 | Le et al. |
| 5,941,882 A | 8/1999 | Jammet et al. |
| 5,944,724 A | 8/1999 | Lizardi |
| 5,944,739 A | 8/1999 | Zlock et al. |
| 5,948,002 A | 9/1999 | Bonutti |
| 5,961,538 A | 10/1999 | Pedlick et al. |
| 5,964,783 A | 10/1999 | Grafton et al. |
| 5,968,044 A | 10/1999 | Nicholson et al. |
| 5,980,557 A | 11/1999 | Iserin et al. |
| 5,980,558 A | 11/1999 | Wiley |
| 5,993,459 A | 11/1999 | Larsen et al. |
| 6,007,566 A | 12/1999 | Wenstrom, Jr. |
| 6,022,373 A | 2/2000 | Li |
| 6,024,758 A | 2/2000 | Thal |
| 6,027,523 A | 2/2000 | Schmieding |
| 6,036,701 A | 3/2000 | Rosenman |
| 6,045,573 A | 4/2000 | Wenstrom, Jr. et al. |
| 6,045,574 A | 4/2000 | Thal |
| 6,066,160 A | 5/2000 | Grossi et al. |
| 6,117,162 A | 9/2000 | Schmieding et al. |
| 6,146,406 A | 11/2000 | Shluzas et al. |
| 6,149,669 A | 11/2000 | Li |
| 6,159,235 A | 12/2000 | Kim |
| 6,168,598 B1 | 1/2001 | Martello |
| 6,179,840 B1 | 1/2001 | Bowman |
| 6,200,329 B1 | 3/2001 | Fung et al. |
| 6,214,031 B1 | 4/2001 | Schmieding et al. |
| 6,306,159 B1 | 10/2001 | Schwartz et al. |
| 6,355,066 B1 | 3/2002 | Kim |
| 6,508,830 B2 | 1/2003 | Steiner |
| 6,517,542 B1 | 2/2003 | Papay et al. |
| 6,544,281 B2 | 4/2003 | ElAttrache et al. |
| 6,656,183 B2 | 12/2003 | Colleran et al. |
| 6,986,781 B2 | 1/2006 | Smith |
| 7,037,324 B2 | 5/2006 | Martinek |
| 2001/0041916 A1 | 11/2001 | Bonutti |
| 2002/0040241 A1 | 4/2002 | Jarvinen |
| 2002/0161401 A1 | 10/2002 | Steiner |
| 2003/0065361 A1* | 4/2003 | Dreyfuss ..................... 606/232 |
| 2003/0088272 A1 | 5/2003 | Smith |
| 2003/0105489 A1 | 6/2003 | Eichhorn et al. |
| 2004/0088004 A1 | 5/2004 | Rosch |
| 2004/0093031 A1 | 5/2004 | Burkhart et al. |
| 2004/0111117 A1 | 6/2004 | Colleran et al. |
| 2004/0133239 A1 | 7/2004 | Singhatat |

FOREIGN PATENT DOCUMENTS

| | | |
|---|---|---|
| EP | 0502509 | 9/1992 |
| EP | 0 574 707 | 12/1993 |
| EP | 0 755 656 | 1/1997 |
| WO | WO 92/04874 | 4/1992 |
| WO | WO 95/29637 | 11/1995 |
| WO | 09620647 | 7/1996 |
| WO | WO 01/67962 | 9/2001 |
| WO | WO 02/36020 | 5/2002 |
| WO | WO 03/047437 | 6/2003 |

OTHER PUBLICATIONS

Panalok Anchor with Panacryl Suture 1997, 2 pages.
Office Action in U.S. Appl. No. 09/986,376 mailed Jan. 21, 2003, 7 pages.
Office Action in U.S. Appl. No. 90/006,989 mailed Dec. 7, 2004, 5 pages.
Office Action in U.S. Appl. No. 90/006,989 mailed May 9, 2005, 8 pages.
Office Action in U.S. Appl. No. 90/006,989, mailed May 20, 2004.
Office Action in U.S. Appl. No. 90/006,989, mailed Dec. 7, 2004.

Office Action in U.S. Appl. No. 90/006,989, mailed May 9, 2005.
Office Action in U.S. Appl. No. 90/006,989, mailed Aug. 16, 2005.
Office Action in U.S. Appl. No. 90/006,989, mailed Aug. 23, 2006.
Office Action in U.S. Appl. No. 90/006,989, mailed Jul. 26, 2007.
USPTO Non-final Office Action in U.S. Appl. No. 10/724,121, mailed Dec. 8, 2005, 13 pages.
USPTO Final Office Action in U.S. Appl. No. 10/724,121, mailed Oct. 25, 2006, 5 pages.
USPTO Non-final Office Action in U.S. Appl. No. 10/724,121, mailed May 4, 2007, 5 pages.
USPTO Reexamination Action in U.S. Appl. No. 90/006,989, mailed Dec. 7, 2004, 6 pages.
USPTO Reexamination Action in U.S. Appl. No. 90/006,989, mailed Aug. 23, 2006, 44 pages.
USPTO Reexamination Action in U.S. Appl. No. 90/006,989, mailed Jul. 26, 2007, 32 pages.

* cited by examiner

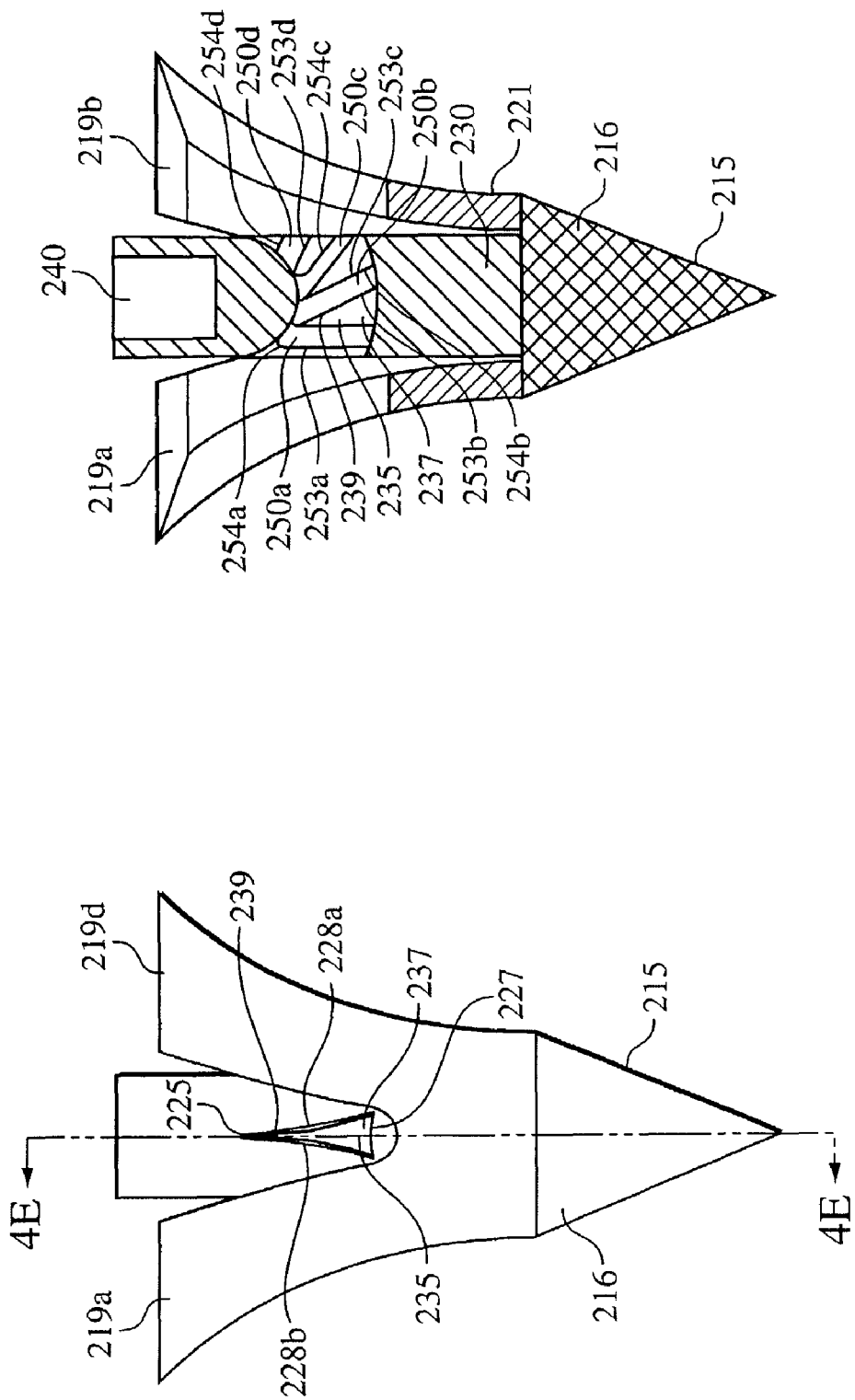

REATTACHMENT OF TISSUE TO BASE TISSUE

CROSS-REFERENCE TO RELATED APPLICATIONS

This application is a continuation-in-part application of and claims priority to U.S. application Ser. No. 09/986,376, filed on Nov. 8, 2001 now U.S. Pat. No. 6,656,183, which is incorporated herein by reference.

TECHNICAL FIELD

This invention relates to reattachment of tissue to base tissue.

BACKGROUND

Fibrous tissues, such as ligaments and tendons, can detach from bone. The detachment can be repaired using sutures. It is known to fix a fibrous tissue to bone by inserting a suture anchor into the bone and knotting suture attached to the anchor to tie down the fibrous tissue to the bone. Tying suture knots in minimally invasive surgical procedures commonly requires a skilled surgeon and/or specialized equipment.

SUMMARY

According to one aspect there is a flexible member anchor. The anchor includes a flexible member and a body. The flexible member has a loop. The body has a channel, through which the flexible member is disposed, and an anchoring mechanism. The channel includes a unidirectional mechanism configured to allow movement of the flexible member through the channel in a first direction and to restrict movement of the flexible member through the channel in a second direction. The anchoring mechanism is configured to anchor the body in base tissue.

The anchor can include other additional features. In one example, the anchoring mechanism can include ridges disposed on an outer surface of the body. The anchoring mechanism can include ridges disposed peripherally body. The anchoring mechanism can also include ridges comprising an edge angled towards an end of the body.

In another example, the channel can include an entrance port and an exit port disposed in an end of the body. The anchor can include a conical shaped feature disposed at another end of the body located opposite the end including the entrance port and the exit port. The flexible member can be a suture. The loop of the flexible member can be a preformed loop.

In another example, the unidirectional mechanism includes a constricting mechanism to constrict the flexible member when traveling in the second direction. The unidirectional mechanism can also include a portion of the channel including a transverse cross section having a tapered diameter and ridges disposed adjacent the portion of the channel, where the ridges are configured to direct the flexible member towards a widest portion of the tapered diameter of the portion of the channel when the flexible member travels in the first direction and towards a narrowest portion of the tapered diameter of the portion of the channel when the flexible member travels in the second direction. The portion of the channel can be linear. The ridges can be disposed parallel to each other. The first direction can be opposite the second direction.

In another example, an end of the anchor body is conical in shape. The anchor can also include an insertion feature configured to accept a tool that enables an operator to apply force to the flexible member anchor to insert the flexible member anchor into base tissue. The insertion feature can be a bore. In another example, the body comprises a substantially rigid material. This can be a biocompatible metal and/or a biocompatible polymer. The flexible member anchor of claim 17 wherein the base tissue comprises bone.

According to another aspect, there is an anchor that includes a body having an axial member with a distal end and a proximal end. The axial member has a channel, through which a flexible member passes. The channel includes a linear channel portion and a first plurality of ridges. The linear channel portion includes a tapered transverse cross section having a wide portion and a narrow portion. The first plurality of ridges form a portion of the linear channel portion and are oriented i) from the wide portion to the narrow portion and ii) not parallel to the tapered transverse cross section. The anchor also includes a second plurality of ridges disposed peripherally on the axial member.

The anchor can include other additional features. In one example, the distal end of the axial member includes a conical shaped element. The second plurality of ridges can include ridges having an angled surface, where the angled surface extends from the distal end towards the proximal end. The channel can include an entrance port and an exit port disposed at the proximal end of the axial member. The anchor can also include an insertion feature defining a cavity disposed at the proximal end of the axial member.

In another example, the anchor includes a flexible member disposed through the channel. The flexible member can be a suture. The flexible member can include a loop. The loop can be a preformed loop. In another example, the anchor includes a substantially rigid material. The rigid material can be a biocompatible metal and/or a biocompatible polymer. In another example, the first plurality of ridges is substantially parallel to each other.

According to another aspect, there is a surgical method. The surgical method includes attaching a flexible member to candidate tissue using a loop and inserting the flexible member into a flexible member anchor. The method also includes attaching the flexible member anchor to base tissue, pulling the flexible member through the flexible member anchor to adjust spacing between the base tissue and the candidate tissue, and maintaining the spacing using a unidirectional mechanism of the flexible member anchor.

The surgical method can include additional features. In one example, the inserting is performed subsequent to attaching the flexible member anchor to base tissue. Attaching the flexible member to the candidate tissue can also include generating a hole in the candidate tissue, passing a portion of the flexible member through the hole to position the loop on one side of the hole and a second end of the flexible member on an opposite end of the hole, and passing the second end of the flexible member through the loop. Passing the second end of the flexible member through the loop can be performed external to a patient's body.

In another example, passing a portion of the flexible member through the hole and passing the second end of the flexible member through the loop can be performed subsequent to inserting the flexible member into the flexible member anchor. Passing the second end of the flexible member through the loop can also include passing the second end of the flexible member including the flexible member anchor through the loop. Generating a hole can also include puncturing the candidate tissue using the flexible member anchor.

In another example, the surgical method can include forming a loop at an end of the flexible member. The flexible member can be a suture. The flexible member can include a preformed loop. The base tissue can include bone.

The details of one or more embodiments of the invention are set forth in the accompanying drawings and the description below. Other features, objects, and advantages of the invention will be apparent from the description and drawings, and from the claims.

DESCRIPTION OF DRAWINGS

FIG. 4D is another side view of the bone anchor of FIG. 4A;

FIG. 4E is a cross-sectional side view of the bone anchor of FIG. 4A taken along lines 4E-4E of FIG. 4D;

DETAILED DESCRIPTION

Figure 1:
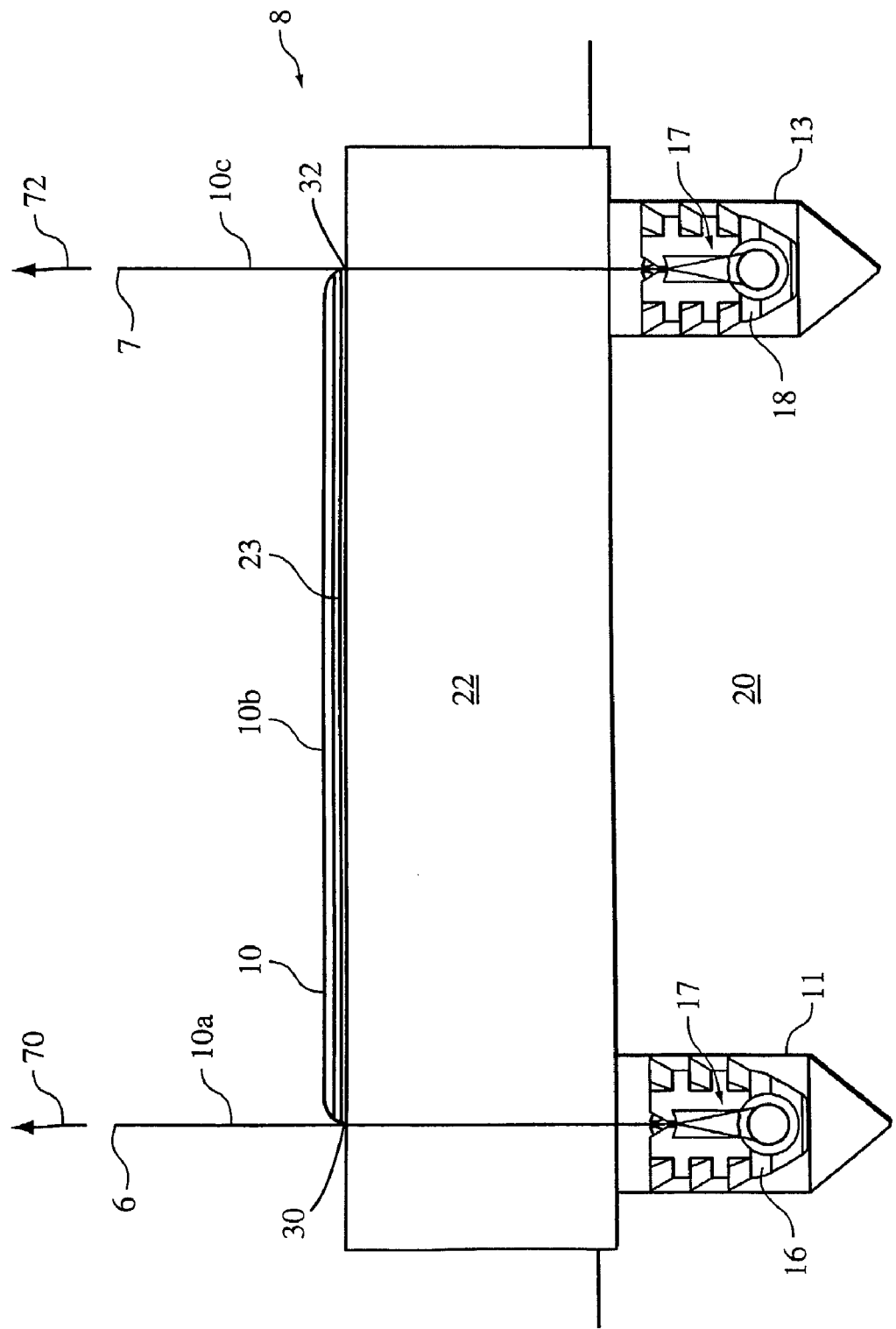
FIG. 1 is a diagrammatic illustration of a system for reattaching fibrous tissue to bone.

Referring to FIG. 1, a tissue repair system 8 for attaching soft tissue 22, e.g., tendon, ligament, or cartilage, to bone 20 includes a flexible member, e.g., suture 10, coupled to first and second bone anchors 16, 18. Suture 10 includes contiguous suture portions 10a, 10b, and 10c. In use, bone anchors 16, 18 are located within holes 11, 13 in bone 20, with first suture portion 10a extending from bone anchor 16 through a hole 30 in tissue 22 to a first suture end 6, second suture portion 10b spanning between bone anchors 16, 18 and lying along an outer surface 23 of tissue 22, and third suture portion 10c extending from bone anchor 18 through a hole 32 in tissue 22 to a second suture end 7.

Bone anchors 16, 18 each include a first engagement system 17 through which suture 10 is threaded. After implantation in bone 20, the physician pulls on one or both of the ends 6, 7 of suture 10 to shorten the length of suture portion 10b, thus securing tissue 22 against bone 20. Engagement systems 17, discussed further below, couple suture 10 to bone anchors 16, 18, and limit possible loosening of tissue repair system 8 following tissue securement.

Figure 2A:
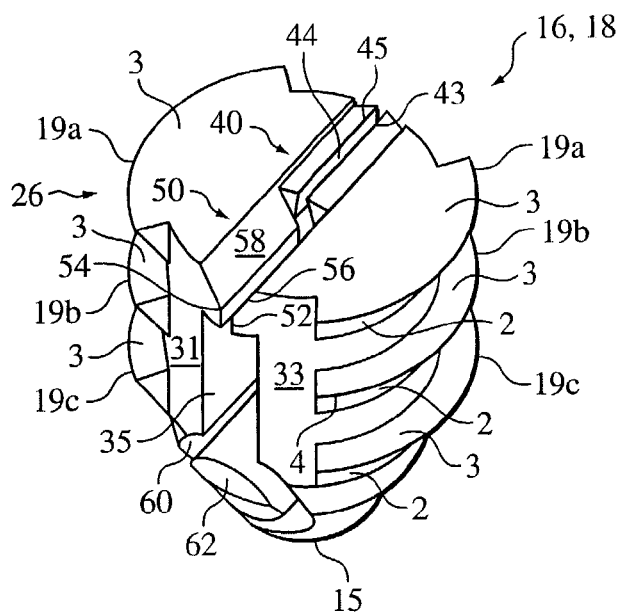
FIG. 2A is a perspective view of a bone anchor.
Figure 2C:
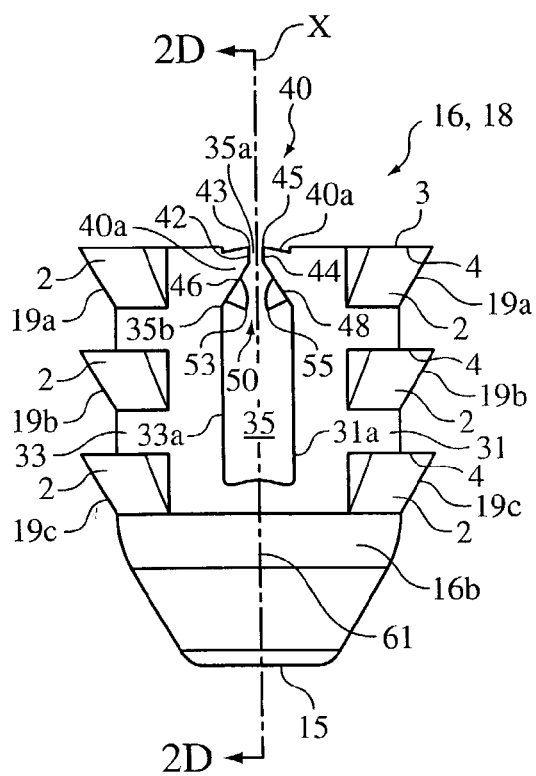
FIGS. 2B and 2C are side views of the bone anchor of FIG. 2A.

Referring to FIG. 2A, bone anchors 16, 18 each have a flat, distal tip 15 and a pair of legs 31, 33 extending proximally from tip 15 to a proximal end 26. Legs 31, 33 are generally part-circular in shape (FIG. 2E) with a region of increased outer diameter defined by a series of radial ridges (here three ridges 19a, 19b, 19c shown) that engage bone tissue to resist the withdrawal of the anchor from the bone hole. Each ridge 19a, 19b, 19c has a sloped distal face 2, a proximal face 3 that is substantially normal to the long axis, X, of bone anchors 16, 18, and a bone engaging edge 4 (FIG. 2B) defined at the intersection of faces 2 and 3.

Engagement system 17 includes a pair of restrictor cleats 40, 50 at the proximal end 26 of legs 31, 33. Legs 31, 33 have inner walls 31a, 33a (FIG. 2B), respectively, that define a slot opening 35 therebetween extending from proximal end 26 to a distal chamber 60. Located within chamber 60 is a winding post 62. The open sides of slot opening 35 provide easy access to winding post 62 to aid in threading suture 10 around post 62, though the sides need not be open. Cleats 40, 50 act to selectively restrict passage of suture 10 through opening 35, as described further below.

Figure 2D:
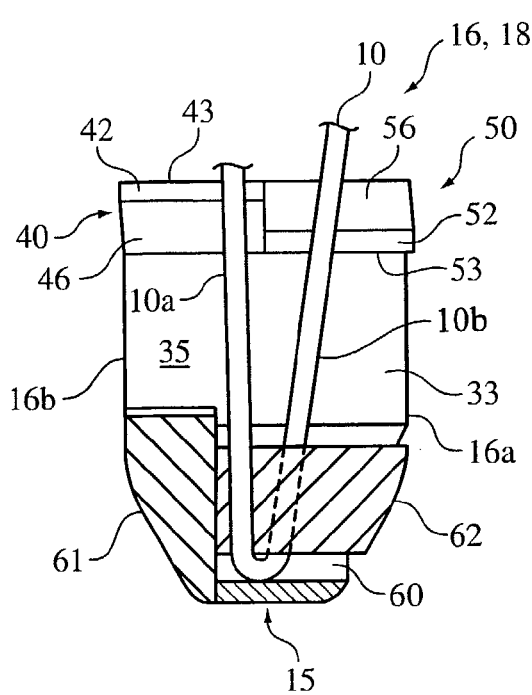
FIGS. 2D is a cross-sectional view of the bone anchor of FIG. 2A taken along lines 2D-2D of FIGS. 2B and 2C.
Figure 2E:
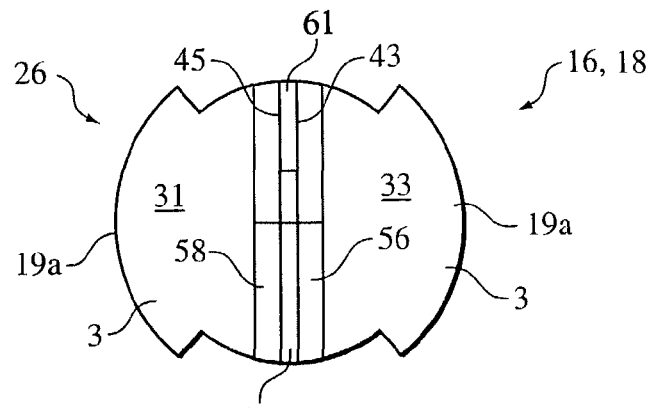
FIGS. 2E and 2F are respectively top and bottom views of the bone anchor of FIG. 2A.

As shown in FIG. 2D, winding post 62 extends into chamber 60 from a wall 61 at a back side 16b of anchor 16. Winding post 62 and wall 61 are tapered inwardly toward distal tip 15 to provide a smooth, tapered distal portion. Chamber 60 circumscribes winding post 62, and is open at a front side 16a of the bone anchor to aid in threading suture 10 through anchor 16. Suture 10 is threaded through anchor 16 such that the suture passes through cleat 50 and opening 35, into interior chamber 60 and around winding post 62, then through opening 35 and cleat 40. Winding post 62 contacts and retains suture 10 within interior chamber 60, and is of sufficient mechanical strength to withstand tension applied to suture 10.

Figure 2B:
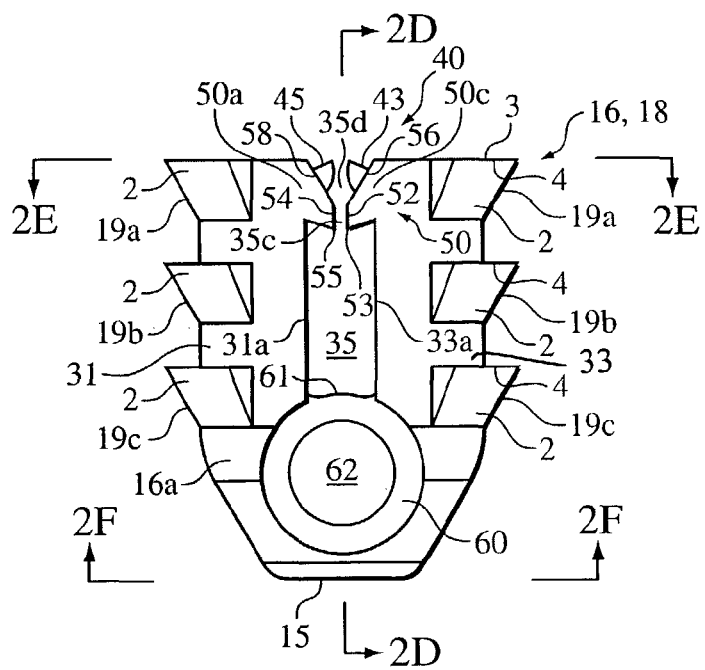
Figure 2F:
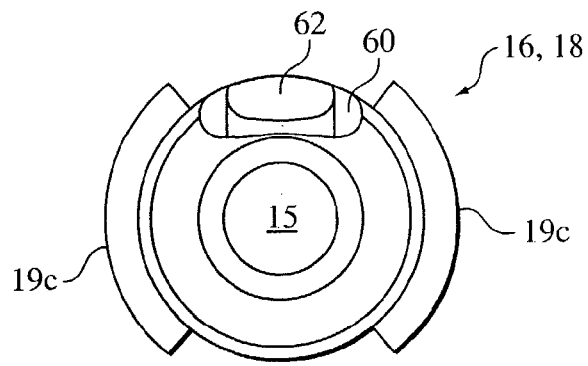

Referring to FIGS. 2B and 2C, cleat 40 is formed by an opposing pair of protrusions 40a having proximal faces 42, 44 that define a narrower portion 35a of channel 35 therebetween, and distal faces 46, 48 that define a wider, sloped portion 35b of channel 35 therebetween. Cleat 50 is oriented opposite of cleat 40 with an opposing pair of protrusions 50a having distal faces 52, 54 that define a narrower portion 35c of channel 35 therebetween, and proximal faces 56, 58 that define a wider, sloped portion 35d of channel 35 therebetween. Proximal faces 42, 44 have opposing edges 43, 45

(defined by the proximal corners of faces 42, 44), and distal faces 52, 54 have opposing edges 53, 55 (defined by the distal corners of faces 52, 54). Each opposing pair of edges 43, 45 and 53, 55 is separated by a separation distance that is substantially equal to or smaller than the diameter of suture 10.

Movement of suture 10 through sloped portions 35b, 35d of cleats 40, 50 acts to compress the suture such that the suture can pass through narrower portions 35a, 35c, respectively, when pulled in the direction of arrow 70 (FIG. 1). However, loosening of suture 10 (passage of suture 10 through the cleats in a direction opposite arrow 70) is limited by opposing edges 43, 45 and 53, 55 catching on uncompressed suture 10 such that the suture does not pass through the cleats. In effect, cleats 40, 50 form a one-way passage.

Referring again to FIG. 1, suture 10 is threaded through anchors 16 and 18 such that from suture end 6, suture portion 10a passes through cleat 40 in anchor 16 to post 62, suture portion 10b extends from post 62 through cleat 50 in anchor 16, then through cleat 50 in anchor 18, to post 62, and suture portion 10c extends from post 62 through cleat 40 in anchor 18 to suture end 7. This permits the suture to pass through the cleats (with the sloped portions of the cleats compressing the suture such that the suture can pass through the narrow portions of the cleats) when ends 6, 7 are pulled in the directions of arrows 70, 72, respectively, to shorten suture length 10b, but resists passage through the cleats (by the opposing edges of the cleats catching on uncompressed suture) when a load tending to lengthen suture length 10b is placed on the suture.

In use, the operator implants first and second bone anchors 16, 18 into, e.g., a predrilled hole in bone 20 through tissue 22 (and an overlaying cartilage layer, if present) by, e.g., applying a compressive or torsional load to members 16, 18 as appropriate. The operator then draws one or both ends 6, 7 of suture portions 10a, 10c in the direction of arrows 70, 72 to shorten the length of suture portion 10b between first and second bone anchors 16, 18. Suture portion 10b draws tissue 22 toward bone 20. The anchors can be supplied to the operator with suture 10 prethreaded to through anchors 16, 18, or the operator can thread suture 10 through the anchors.

When suture portion 10b is sufficiently taut, the operator releases and/or cuts the free ends of the suture extending from the soft tissue. Although, during healing, a patient may apply forces that tend to draw tissue 22 away from bone 20, engagement systems 17 resist the lengthening of suture portion 10b. In particular, cleats 40, 50 restrict passage of the suture portion 10c in the direction opposite to arrow 72 and suture portion 10a in the direction opposite to arrow 70. Moreover, cleats 40, 50 engage and restrict the passage of suture 10 at a substantially arbitrary position along the length of suture 10. In other words, there is no need, e.g., to clamp suture 10 with another member, or have an enlarged portion such as a knot in suture 10 to restrict the passage of suture 10 through the cleats. Cleats 40, 50 thus selectively restricts movement of suture 10 by allowing the passage of suture 10 through the cleats in a first direction while subsequent passage of suture 10 in a second, opposite direction is restricted.

Figure 3A:
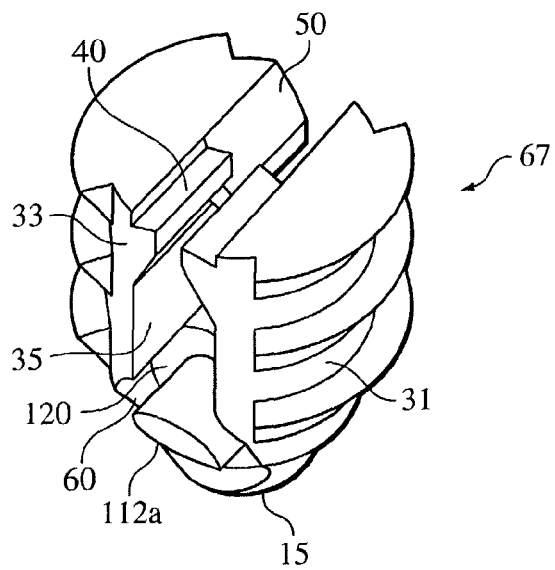
FIG. 3A is a perspective view of an alternative embodiment of a bone anchor.
Figure 3B:
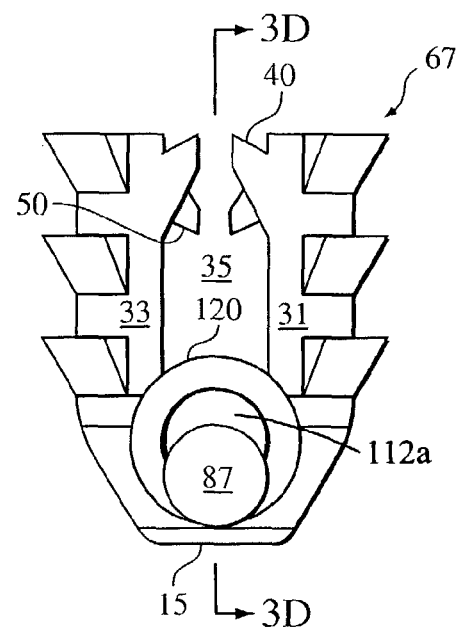
FIGS. 3B and 3C are side views of the bone anchor of FIG. 3A.
Figure 3D:
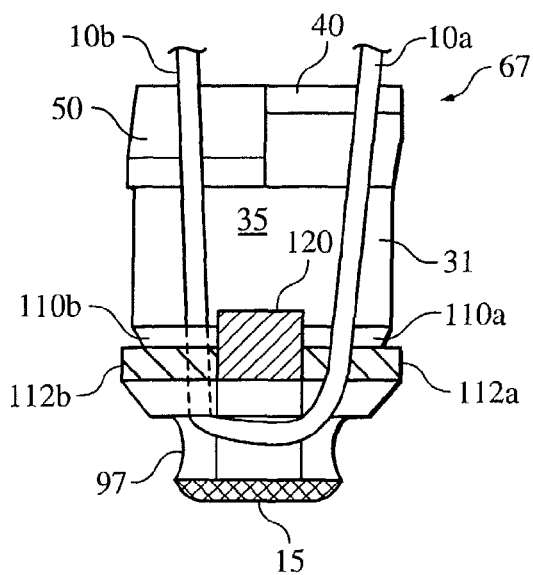
FIG. 3D is a cross-sectional view of the bone anchor of FIG. 3A taken along lines 3D-3D of FIGS. 3B and 3C.
Figure 3E:
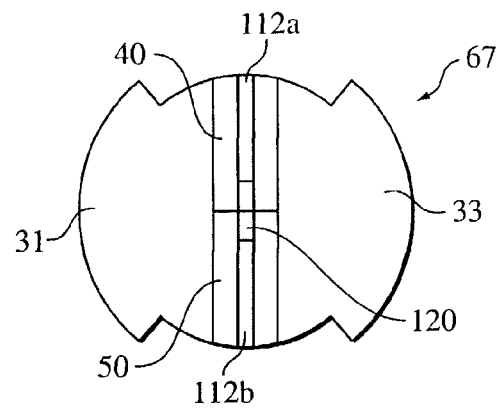
FIGS. 3E and 3F are respectively top and bottom views of the of the bone anchor of FIG. 3A.
Figure 3C:
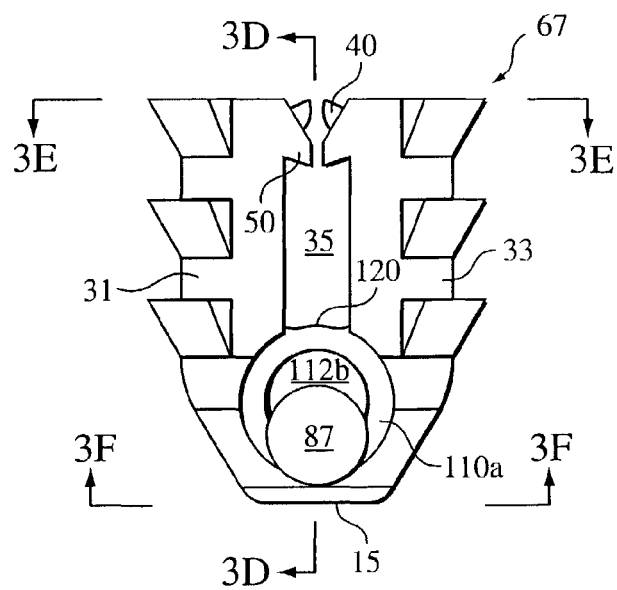
Figure 3F:
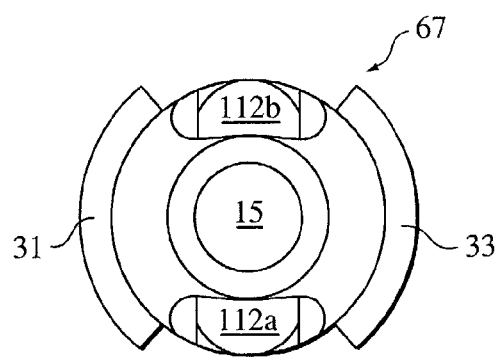
Figure 3G:
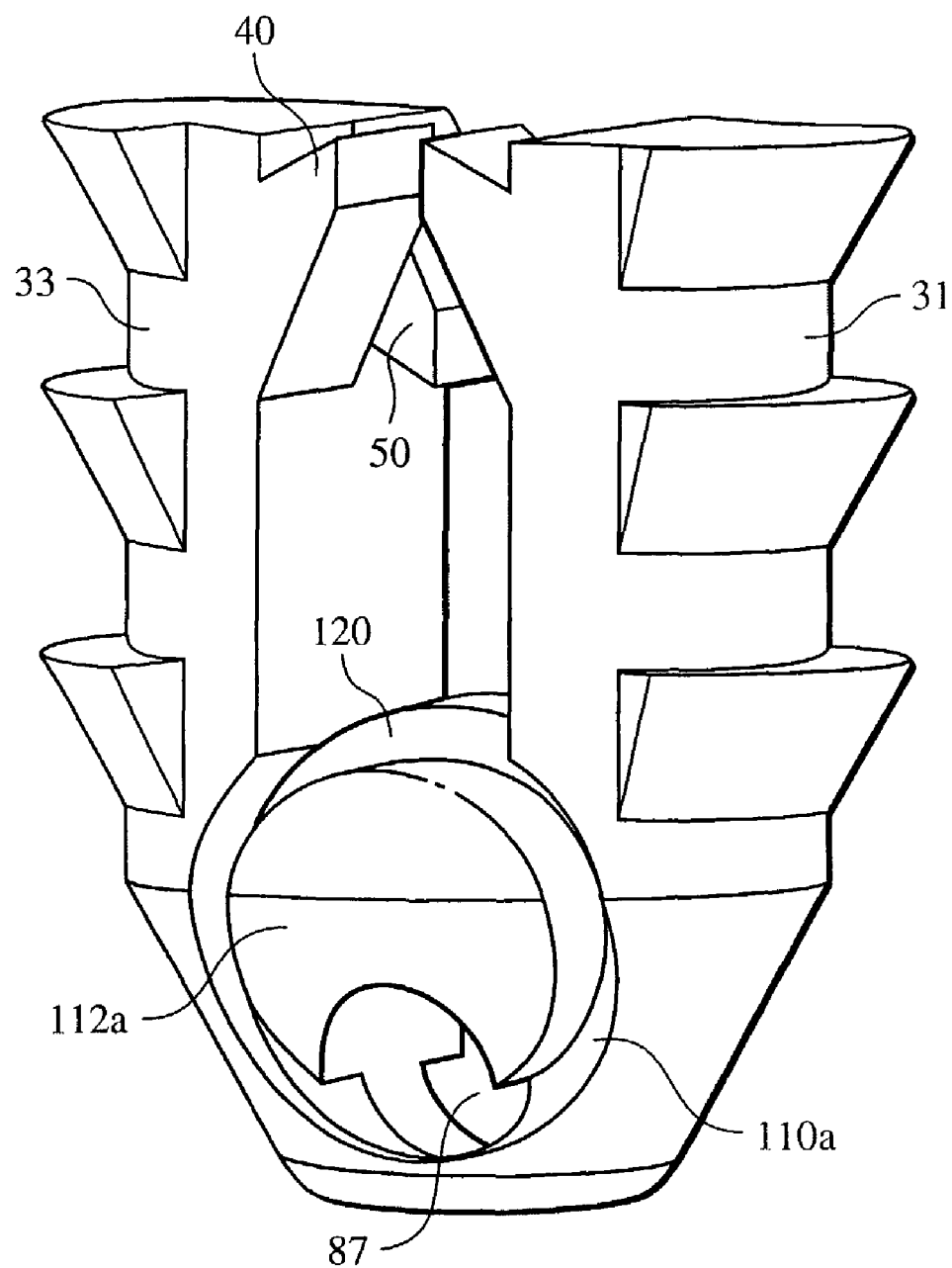
FIG. 3G is another perspective view of the bone anchor of FIG. 3A.

Other embodiments are within the scope of the following claims. For example, referring to FIGS. 3A-3F, particularly to FIGS. 3A and 3D, rather than a post 62 extending from a side wall, an alternate bone anchor 67 includes a central member 120 with side posts 112a, 112b located in chamber 60. Side posts 112a, 112b taper inwardly to provide a smooth, tapered distal portion. The outer dimension of side posts 112a, 112b is less than the diameter of chamber 60 such that channels 110a, 110b, respectively, are formed about side posts 112a, 112b, while the outer diameter of central member 120 is equal to the diameter of chamber 60. Posts 112a, 112b and central member 120 defines a transverse passage 87 (FIG. 3G) for passage of suture from channel 110a to 110b. Side posts 112a, 112b have a half-moon shape such that a circular suture passage 87 is formed. Other side posts shapes are possible. Suture 10 passes through cleat 40 to channel 35, to channel 110a and around post 112a to passage 87, through passage 87, to channel 110b around post 112b to channel 35, and through cleat 50.

Figure 4A:
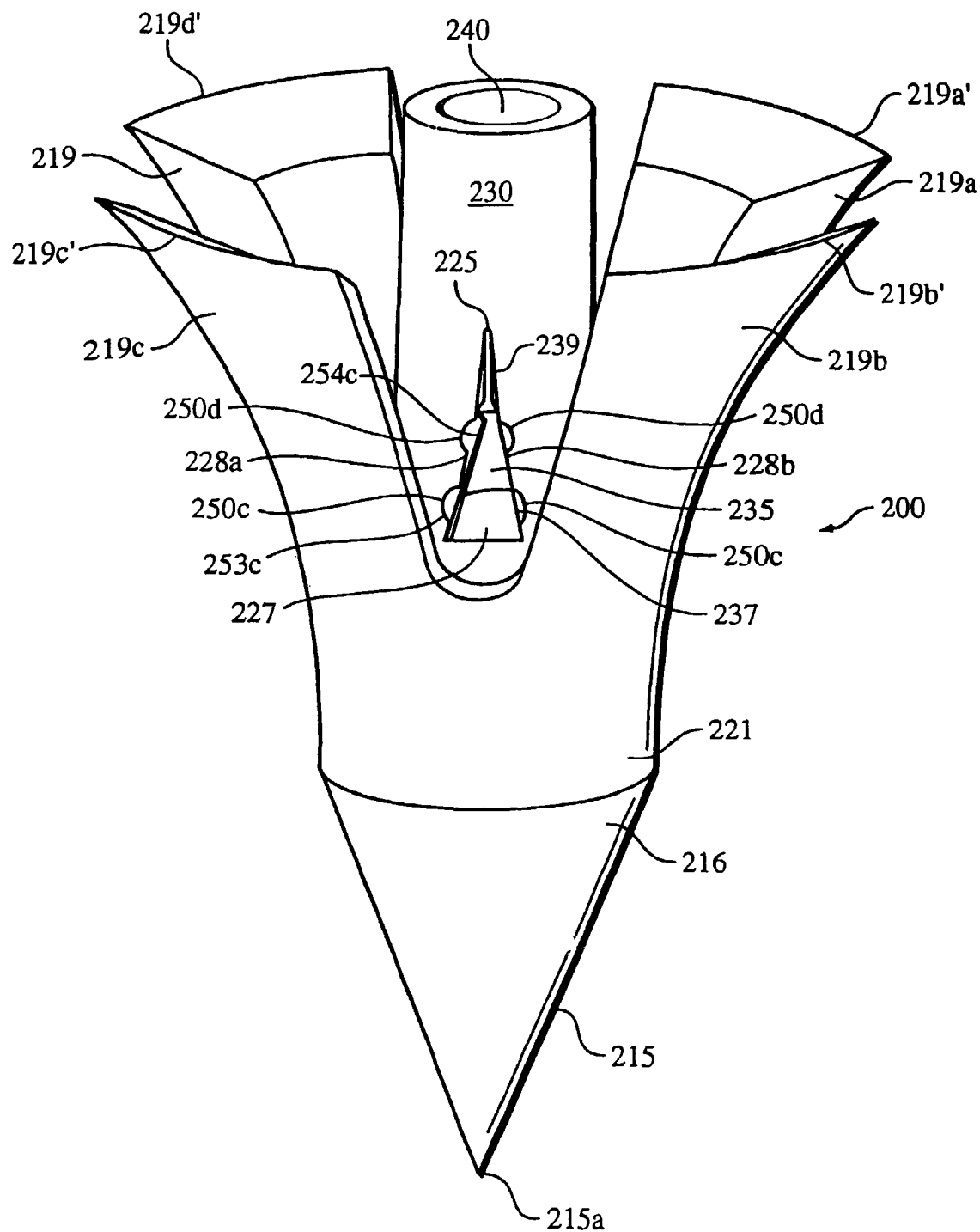
FIG. 4A is a perspective view of another alternative embodiment of a bone anchor.

Referring to FIG. 4A, a bone anchor 200 includes a central member 230, a distal tip 215, and a series of proximally extending, radial wings 219a, 219b, 219c, 219d surrounding central member 230. Central member 230 includes a restrictor in the form of a suture guiding through channel 235 that selectively restricts passage of suture therethrough, as described below. Distal tip 215 is conical in shape and has a tissue penetrating point 215a. Radial wings 219a, 219b, 219c, 219d are joined at a distal end 221 of the wings to a proximal end 216 of distal tip 215, and resiliently flare outwardly from central member 230 in a proximal direction. Each wing has a sharp proximal edge 219a', 219b', 219c', 219d' for digging into bone tissue to resist withdrawal of anchor 200 from the bone. Wings 219a, 219b, 219c, 219d are inwardly deformable toward central member 230 in response to radial compression, such as during insertion into a generally circular opening or hole in bone formed, e.g., by insertion of distal tip 215 into the bone. Central member 230 defines a proximal opening 240 for receiving a drive tool, not shown, for pounding anchor 200 into bone.

Figure 4C:
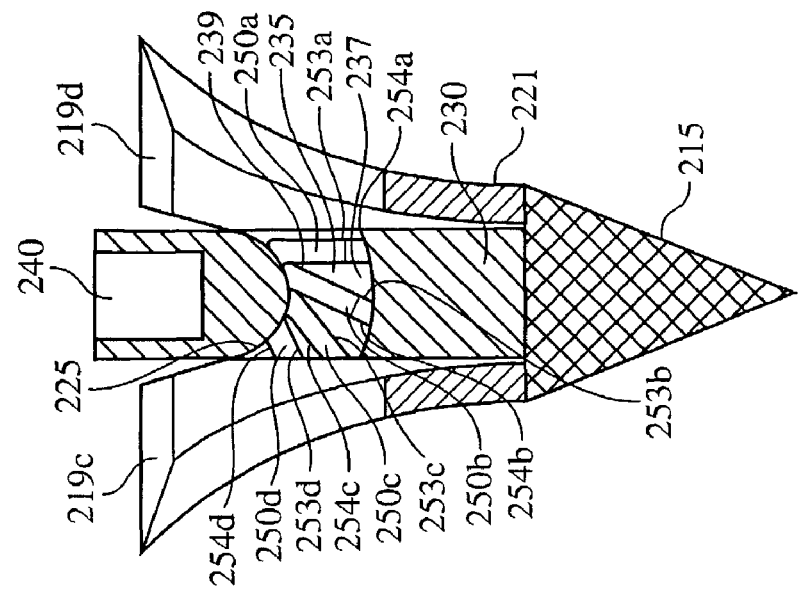
FIG. 4C is a cross-sectional side view of the bone anchor of FIG. 4A taken along lines 4C-4C of FIG. 4B.
Figure 4B:
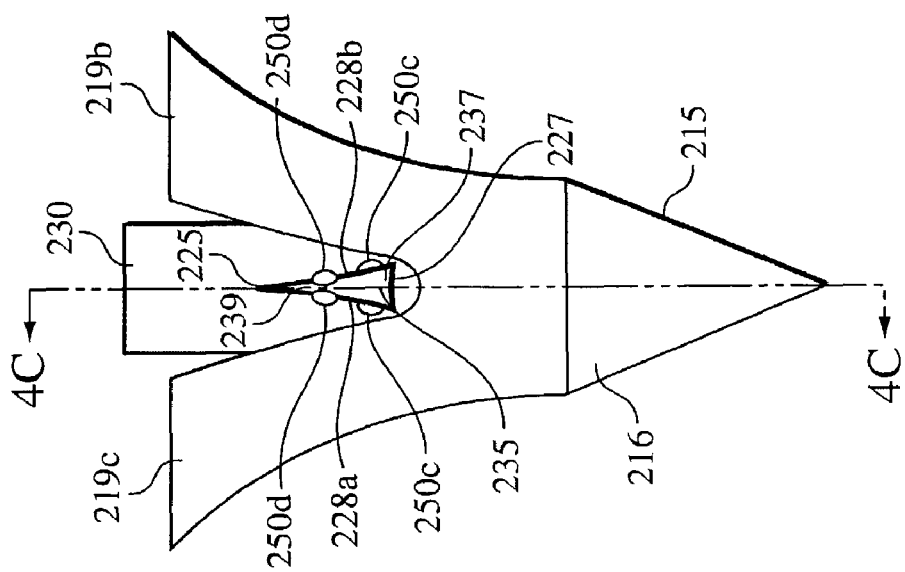
FIG. 4B is a side view of the bone anchor of FIG. 4A.
Figure 4G:
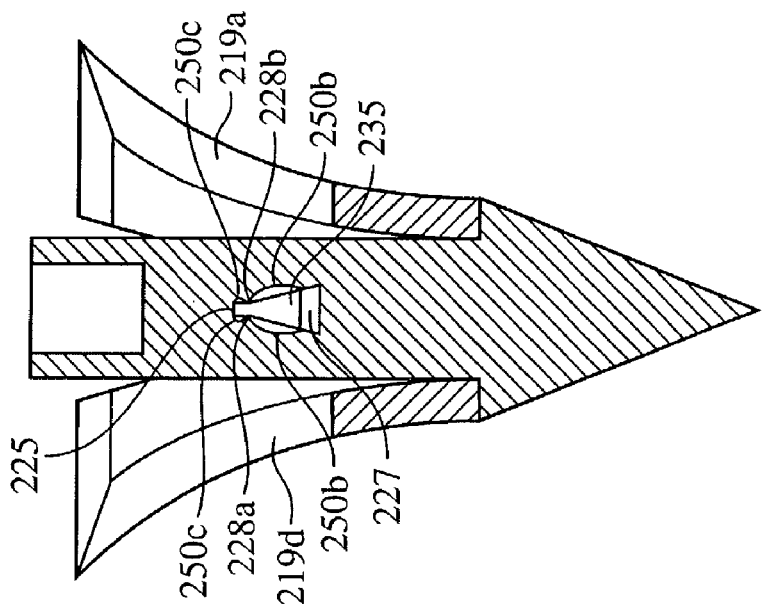
FIG. 4G is a cross-sectional side view of the bone anchor of FIG. 4A taken along lines 4G-4G of FIG. 4F.
Figure 4F:
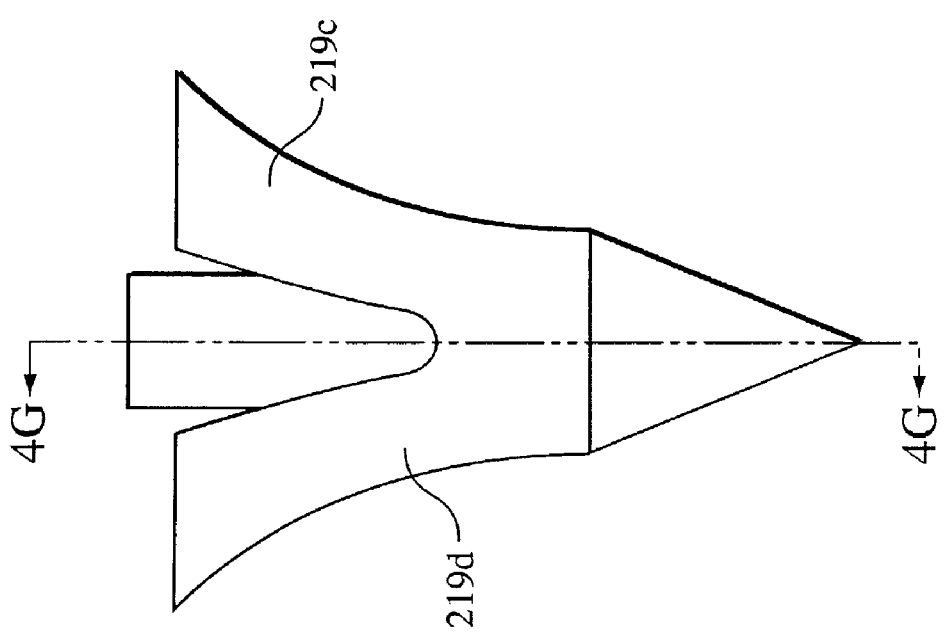
FIG. 4F is another side view of the bone anchor of FIG. 4A.

Referring to FIGS. 4B-4G, suture guiding channel 235 has a generally triangular cross-section with a proximal apex 225, a distal base face 227, and a pair of side faces 228a, 228b. Side faces 228a, 228b converge proximally forming a distal portion 237 of channel 235 that is wider than the diameter of the suture, such that the suture can pass freely therethrough, and a proximal restricting portion 239 of channel 235 that is narrower than the suture diameter to restrict passage of the suture therethrough. Referring particularly to FIGS. 4C and 4E, base face 227 follows an arcuate path through central member 230, as does apex 225 at the intersection of side faces 228a, 228b. As illustrated, the radius of curvature of the path of apex 225 though central member 230 is approximately equal to one half the diameter of central member 230. The curvature of apex 225 presents an atraumatic surface for the suture to rest against when pulled taught, as discussed below.

Figure 5:
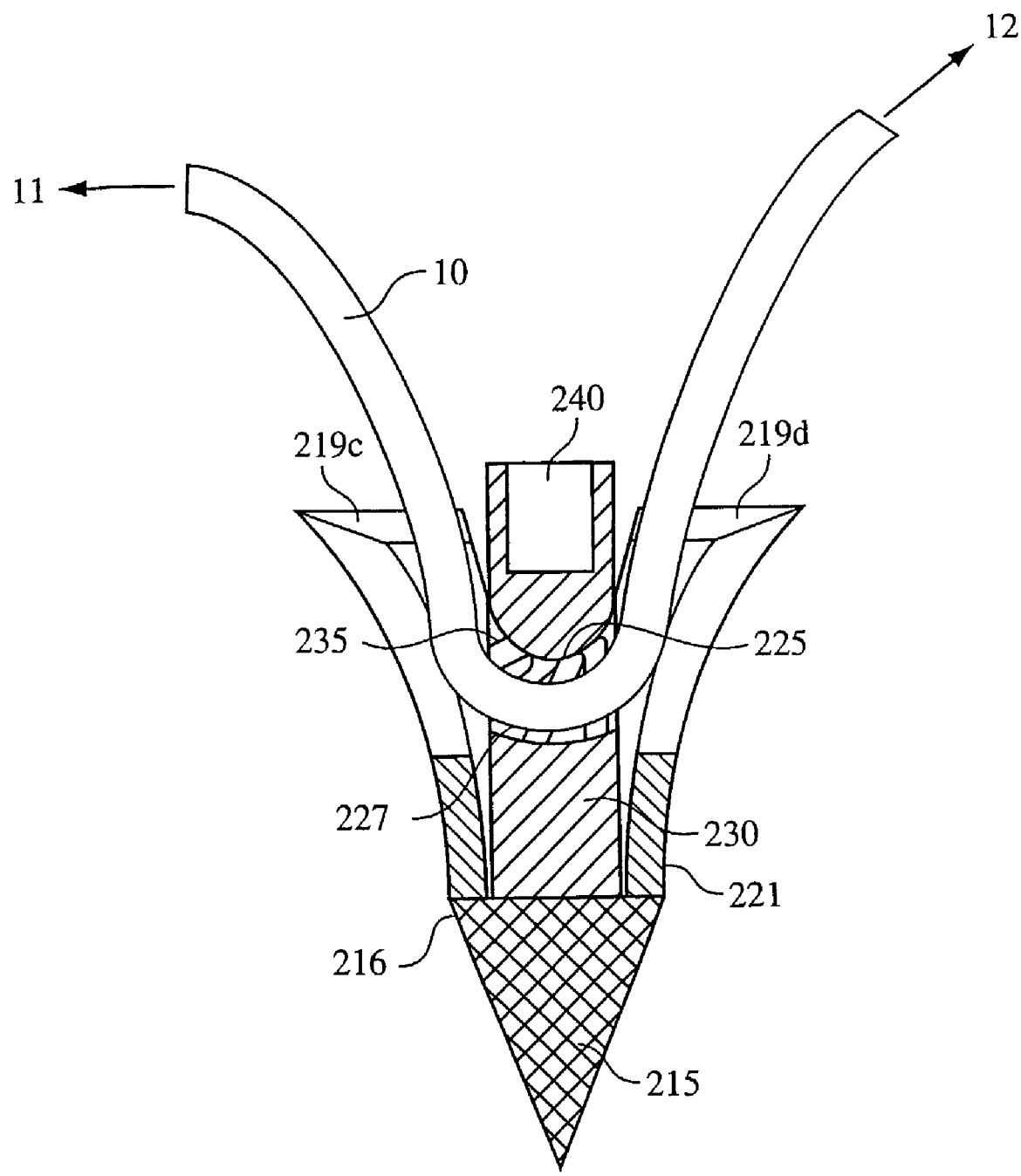
FIG. 5 is a cross-sectional side view of the bone anchor of FIG. 4A shown with a suture coupled thereto.

Side faces 228a, 228b are each lined by a series of grooves 250a, 250b, 250c, 250d. Though four grooves are shown, one or more grooves can be employed. As illustrated, grooves 250a, 250b, 250c, 250d are relatively uniformly oriented with respect to base face 237 and apex 225 of channel 235 such that the grooves have the same oblique angle relative to a suture passing through channel 235, as shown in FIG. 5. Each groove 250a-250d has a first edge 253a-253d, respectively, and a second edge 254a-254d, respectively, oriented generally parallel to the respective first edge and obliquely relative to the passage of suture 10 through channel 235.

Edges 253a-253d and 254a-254d, along with the shape of channel 235, act to permit suture to be pulled in a first direction while limiting movement of the suture in a second opposite direction. Referring to FIGS. 4C and 5A, when suture 10 is pulled in the direction of arrow 11, contact of suture 10 with edges 253a-253d pushes suture 10 in a direction non-parallel to the direction of travel of suture 10 through channel 235. The action of edges 253a-253d upon suture 10 moves suture 10 toward base face 227 into distal channel portion 237, allowing suture 10 to pass through channel 235. When suture 10 is pulled in the direction of arrow 12, contact of suture 10 with edges 254a-254d pushes suture 10 in a direction non-parallel to the direction of travel of suture 10 through channel 235. The action of edges 254a-254d upon suture 10 moves suture 10 toward apex 225 into proximal restricting portion 239, which acts to compress suture 10 and restrict passage of suture 10 through channel 235.

Figure 6:
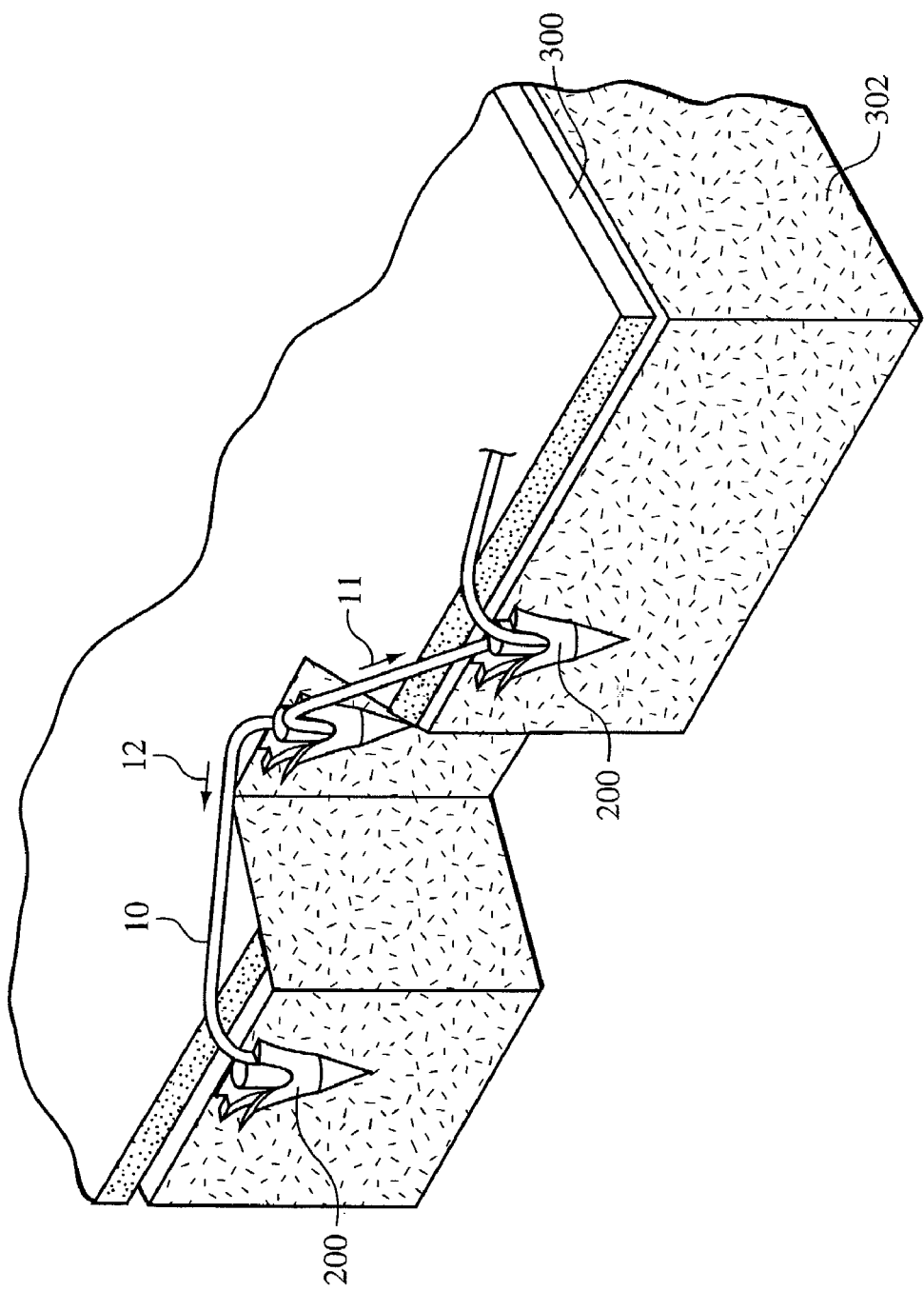
FIG. 6 illustrates the bone anchor of FIG. 4A in use.

Referring to FIG. 6, one or more anchors 200 with suture 10 prethreaded through channel 235 can be deployed through tissue 300 into bone 302. During deployment, wings 219a-219d are initially compressed as they pass through corticol bone, and then expand into the cancellous bone to retain anchors 200 in the bone. By moving suture 10 in the direction of arrow 11, the length of suture between two anchors 200 can be shortened, pulling suture 10 taught, while any tendency of the suture to loosen is limited by movement of suture 10 into proximal restricting portion 239 of channel 235 in response to tension applied to suture 10 in the direction of arrow 12. Suture guiding channel 235 and edges 253a-253d and 254a-254d in anchor 200 thus selectively restricts movement of suture 10 by allowing the passage of suture 10 through portion 237 of channel 235 in a first direction, while restricting subsequent passage of suture 10 in a second, opposite direction by engaging suture 10 in apex 225 at a substantially arbitrary position along the length of the suture 10, without the need for an enlarged portion such as a knot in the suture.

Figure 7A:
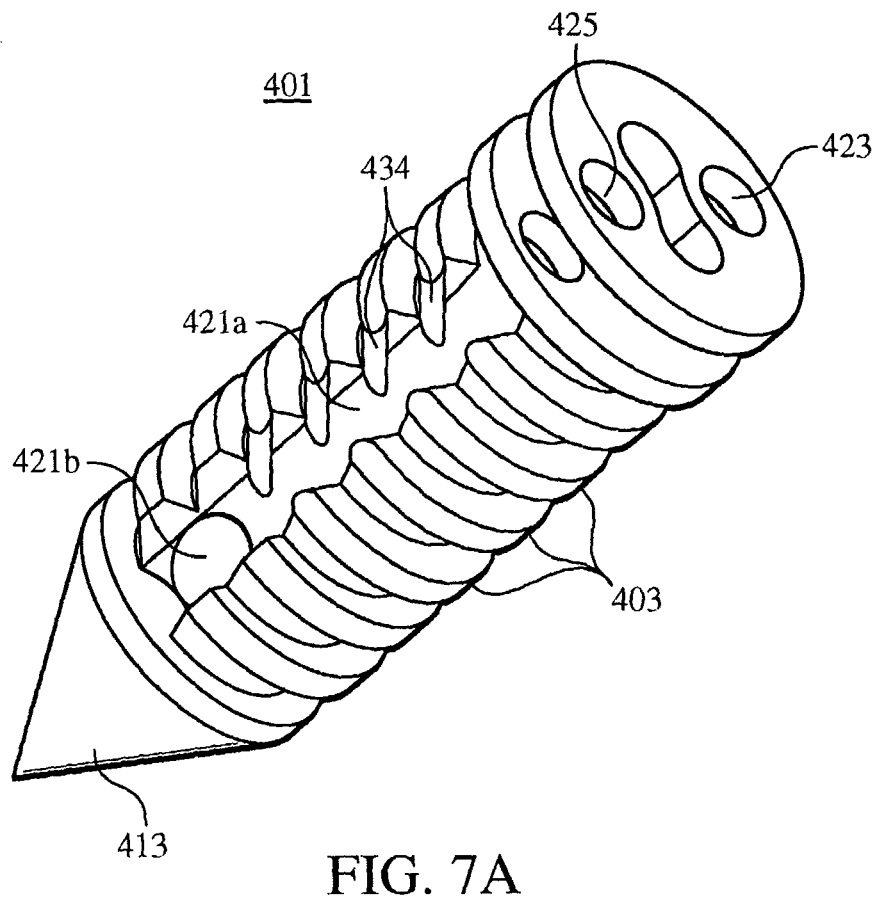
FIG. 7A is a perspective view of another alternative embodiment of an anchor.
Figure 7B:
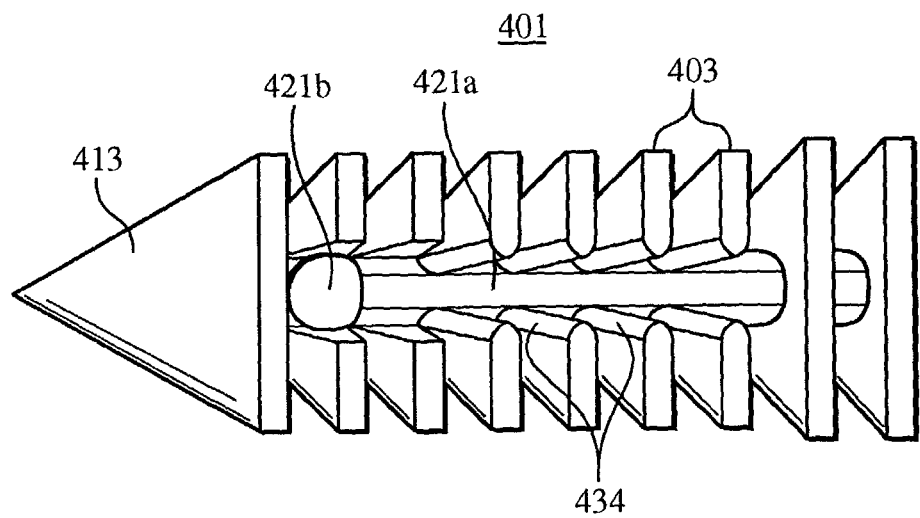
FIG. 7B is a side view of the anchor of FIG. 7A.

FIGS. 7A-B illustrate two views of an anchor 401, which is configured slightly differently from the example anchors above. In general overview, anchor 401 is generally cylindrical in shape with a conical point 413 at its tip to penetrate into tissue. To help hold anchor 401 in place when inserted into base tissue, such as bone, anchor 401 includes ridges 403. Ridges 403 are configured such that when anchor 401 is inserted into the base tissue, anchor 401 easily advances in a direction toward its pointed tip 413 and resists withdrawal from a bone hole in an opposite direction. To insert anchor 401 into the base tissue, a doctor, or other medical personnel performing a procedure, can insert an insertion device into feature 432 and use the insertion device to push anchor 401 into the base tissue. The doctor uses anchor 401 to hold candidate tissue (e.g., tendon, ligament, cartilage and/or the like) adjacent the base tissue into which anchor 401 is inserted. To hold the candidate tissue in place, the doctor attaches a flexible member, such as suture, to the candidate tissue and also attaches the suture to anchor 401. Once the doctor inserts anchor 401 into place in the bone, the doctor tightens the suture, bringing the candidate tissue down to the surface of the bone with the desired tension to complete the repair.

Anchor 401 is configured with a channel 421 to receive the suture. As illustrated, channel 421 has channel portions 421a and 421b. A suture passes through opening 425, through channel portion 421a and through channel portion 421b. The suture continues through another channel portion (not shown, but identified as 421c in FIG. 8A) and through opening 423. The other channel portion 421c not shown in FIGS. 7A and 7B is open (i.e., not totally enclosed), similar to portion 421a, and runs substantially parallel to portion 421a.

One difference between portions 421a and 421c is that channel portion 421a includes a unidirectional mechanism that restricts the direction that the suture can travel through channel 421. As described in more detail below, channel portion 421a includes ridges 434 that selectively restrict passage of a suture through channel 421 so that the suture can travel freely when moving in a direction into opening 423, through channel 421 and out of opening 425, but is restricted and eventually prevented from moving in an opposite direction.

Figure 8A:
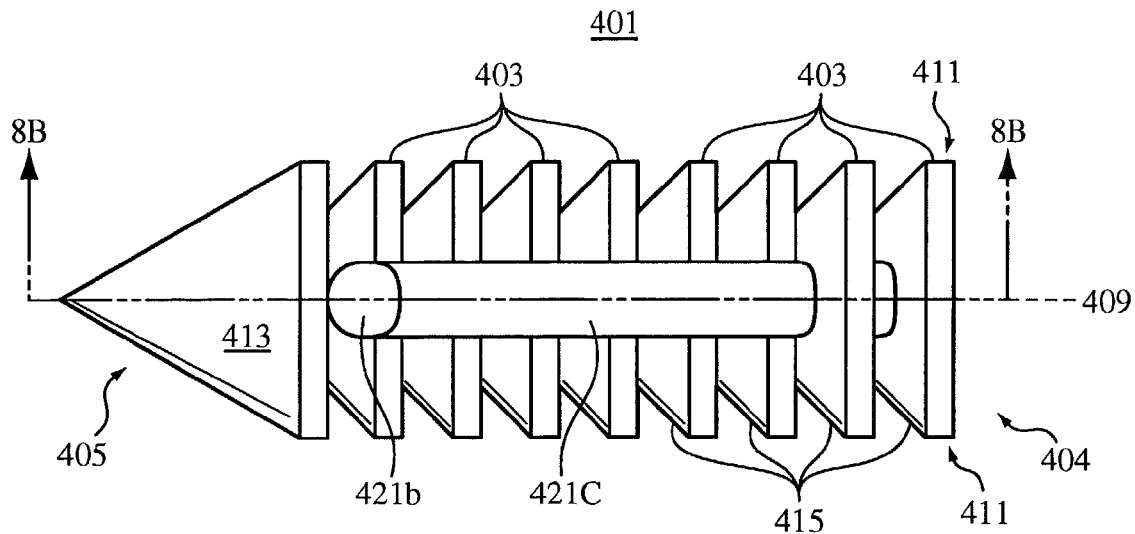
FIG. 8A is another side view of the anchor of FIG. 7A.

FIGS. 8A-D illustrate anchor 401 in more detail. Referring to FIG. 8A, anchor 401 includes a proximal end 404, a distal end 405, a central axis 409, and an outer, peripheral portion 411. Conical point 413 is located at the distal end 405 of anchor 401. As described above, point 413 allows for penetration into soft tissue and/or bone. Other penetration points, like those described above, can also be used. Also as described above, ridges 403 are configured so that when anchor 401 is inserted into base tissue, anchor 401 more easily advances in a direction toward its distal end 405 and resists withdrawal from a bone hole in a direction toward its proximal end 404. To provide this feature, anchor ridges 403 have surfaces 415 that taper toward central axis 409 from distal end 405 toward proximal end 404. In one example anchoring mechanism, the diameter of anchor 401, including ridges 403, is 3.5 mm. Also described above, to receive the suture, anchor 401 includes channel 421 through which the suture passes. At the end of channel portion 421a, closest to distal end 405, there is a curved channel portion 421b in anchor 401 that extends generally transversely through central axis 409.

Figure 8B:
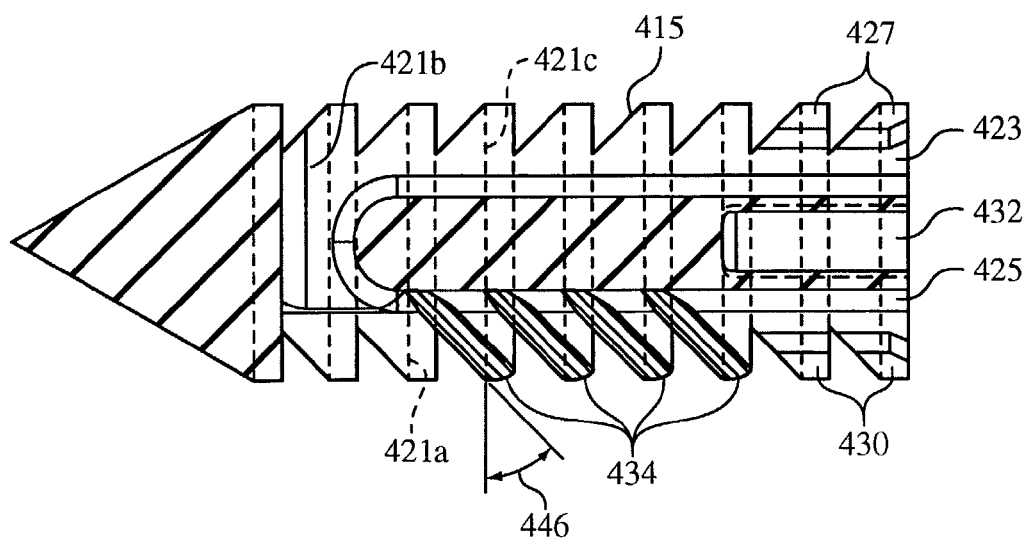
FIG. 8B is a cross-sectional view of the anchor of FIG. 7A taken along lines 8B-8B of FIG. 8A.

FIG. 8B illustrates a cross section of side view FIG. 8A, looking up at the bottom of anchor 401. As illustrated, on the other side of channel portion 421b, there is another channel portion 421c. Channel portions 421a and 421c extend along the sides of anchor 401 from the openings of channel portion 421b to proximal end 404. Where channel portions 421a and 421c meet proximal end 404, there are openings 423 and 425 of the channel portions 421a and 421b, respectively. Small material bridges 427 and 430 define openings 423 and 425, respectively, and complete the circumferential enclosure of channel openings 423 and 425. Also at proximal end 404, there is a feature 432 that is configured to receive a corresponding feature on the distal end of an insertion instrument.

Channel portions 421a and 421c are generally linear and parallel to central axis 409 of anchor 401. Channel portion 421c is semicircular in transverse cross-section. Openings 423 and 425 are circular in transverse cross-section, as shown in more detail in FIG. 7D. Channel portion 421c and openings 423 and 425 are sized to allow free sliding passage of a suture. Channel portion 421a, however, is configured slightly different. As described above, channel portion 421a comprises a unidirectional mechanism to selectively restrict passage of a suture through channel 421. In the illustrated example, channel portion 421a includes ridges 434 that selectively restrict passage of a suture, as described in more detail below.

Figure 8C:
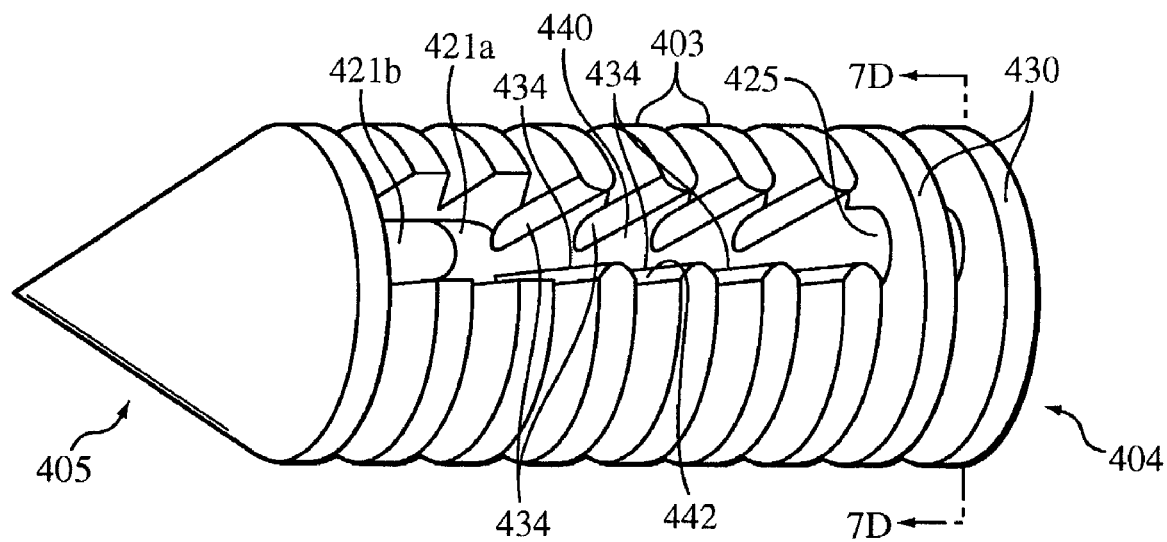
FIG. 8C is a perspective view of the anchor of FIG. 7A.
Figure 8D:
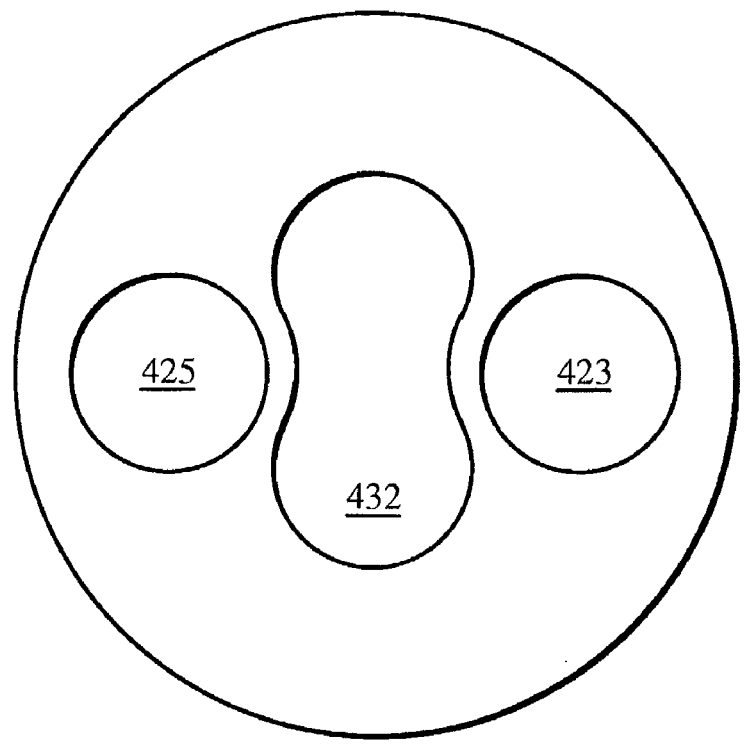
FIG. 8D is a cross-sectional view of the anchor of FIG. 7A taken along lines 8D-8D of FIG. 8C.

Referring to FIG. 8C, channel 421a includes tapered or flared opposing walls 440 and 442 which are more open at the outer surface 411 of anchor 401 and become closer to each other as they become closer to central axis 409. The character of this flare in the channel walls is such that a suture of a given diameter can pass freely when located in the outer, more open portion of the channel (e.g., wide portion 460 of FIG. 9B), and is somewhat constricted when located in the inner, more closed portion of the channel (e.g., narrow portion 462 of FIG. 9C).

Ridges 434, or other such features, are located on opposing sides 440 and 442 of channel portion 421a. Ridges 434 are generally arranged at an angle (e.g., 446, FIG. 8B) to the transverse plane of anchor 401 (i.e., with respect to central axis 409). In other words, the ridges are not parallel the transverse plane of the anchor 401. The angle that each ridge 434 makes with central axis 409 is such that the portion of a ridge 434 closest to central axis 409 in channel portion 421a is closer to distal end 405 than the portion of the ridge 434 that is closest to proximal end 404.

The heights of ridges 434 and their placement within channel portion 421a is such that a suture can slide freely when it is passing more closely to the outer surface 411 of anchor 401 and the suture is constricted from sliding when it is wedged more closely to central axis 409 of anchor 401 within channel portion 421a. Angle 446 is also such that tension placed on the suture which attempts to advance the suture in a distal direction within channel portion 421a causes the suture to be wedged between the ridges 434 more closely to the central axis 409 of channel potion 421a. In some examples, because a portion of channel portion 421a containing ridges 434 is linear, ridges 434 are substantially parallel to each other and their dimensions are substantially identical (within manufacturing tolerances). In one example, angle 446 is in the range of thirty to sixty degrees.

Figure 9A:
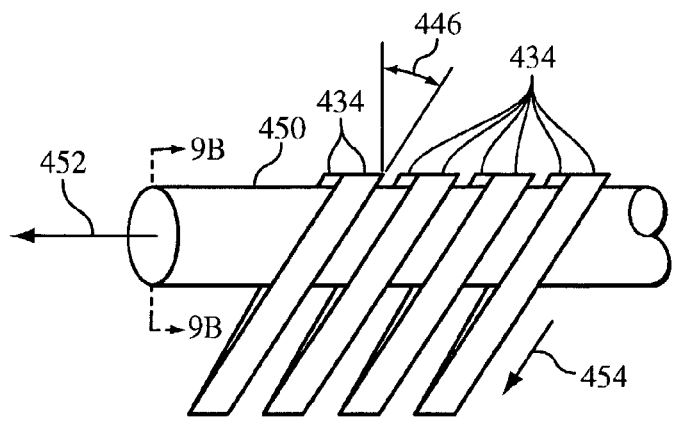
FIG. 9A is a perspective view of a portion of the channel of the anchor.
Figure 9B:
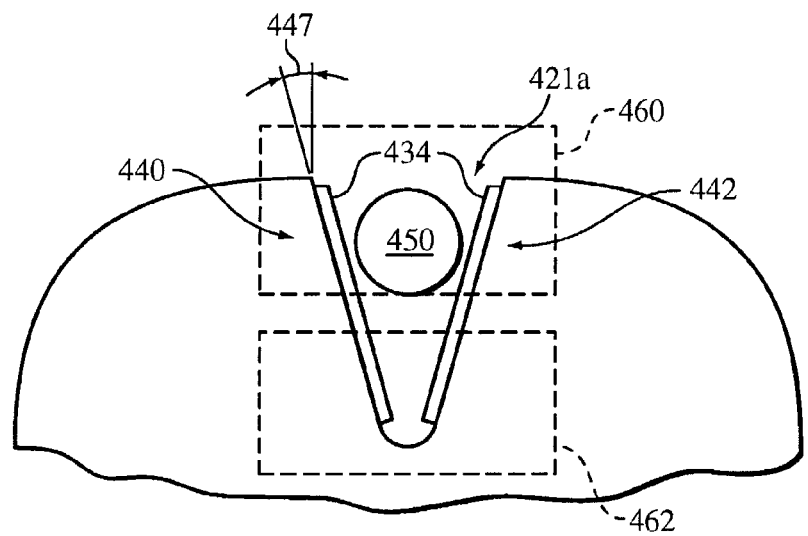
FIG. 9B is a cross-sectional front view of the portion of the channel of FIG. 9A taken along lines 9B-9B of FIG. 9A.
Figure 9C:
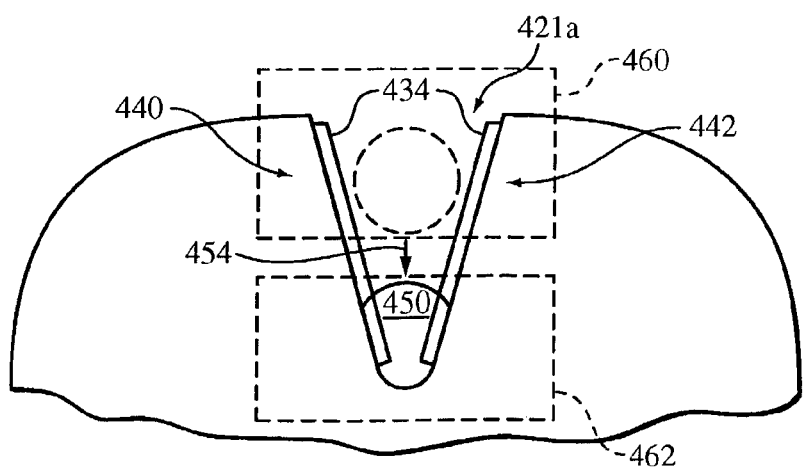
FIG. 9C illustrates the cross-section view of FIG. 9B in an alternate state.

FIGS. 9A-C further illustrate the operation of the unidirectional mechanism as described above. Referring to FIG. 9A, suture 450 travels in a direction indicated by arrow 452. As suture 450 travels in the direction indicated by arrow 452, ridges 434 guide suture 450 in a downward direction, indicated by arrow 454. Ridges 434 guide suture 450 downward because of their angle 446. If suture 450 travels in a direction that is opposite of the direction indicated by arrow 452, ridges 434 guide suture 450 in a upward direction, opposite that indicated by arrow 454. In other words, suture 450 follows the ridges 434 in an up and down direction (e.g., direction indicated by arrow 454) based on the axial direction (e.g., direction indicated by arrow 452) of suture 450.

Referring to FIG. 9B, channel portion 421a tapers and has a wide portion 460 and a narrow portion 462. The angle 447 of the taper, with respect to a vertical axis, is four to twenty degrees. The size of wide portion 460 is such that suture 450 can freely pass therethrough. The size of narrow portion 462 is such that suture 450 cannot freely pass therethrough and is constricted. In other words, narrow portion 462 restricts/prevents motion of suture 450 when the suture is positioned in narrow portion 462 of channel 421. In one example, the width of narrow portion 462 is 25% to 50% of the diameter of the suture. Referring to FIG. 9C, as suture 450 travels in the direction indicated by arrow 452, ridges 434 guide suture 450 in a downward direction, indicated by arrow 454, from wide portion 460 to narrow portion 462. As shown, the size of narrow portion 462 is smaller than suture 450 and ridges 434 constrict suture 450, which prevents further motion in the direction indicated by arrow 452. If suture 450 travels in a direction that is opposite of the direction indicated by arrow 452, ridges 434 guide suture 450 in a upward direction, opposite that indicated by arrow 454, back to wide portion 460 of channel 460, where suture 450 can move freely. The configuration of ridges 434 selectively restricts the motion of suture 450, allowing only free movement in a direction opposite that indicated by arrow 452.

Figure 10A:
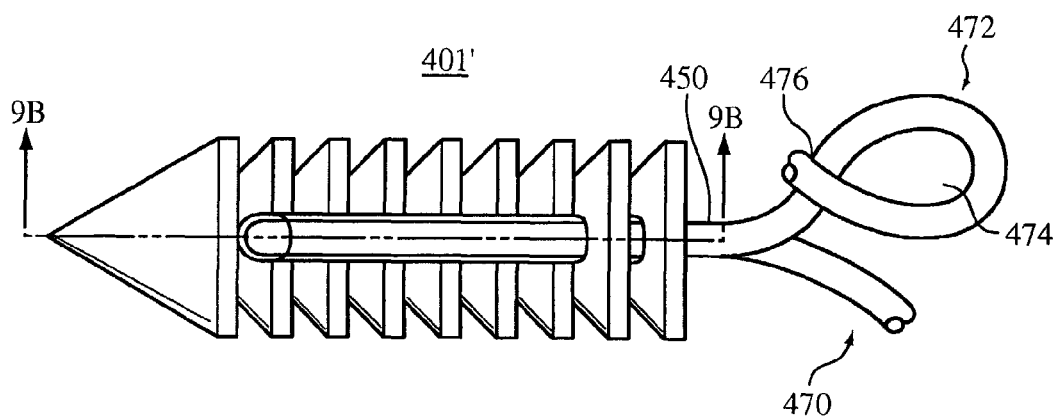
FIGS. 10A and 10B illustrate views 8A and 8B, respectively, with flexible members.
Figure 10B:
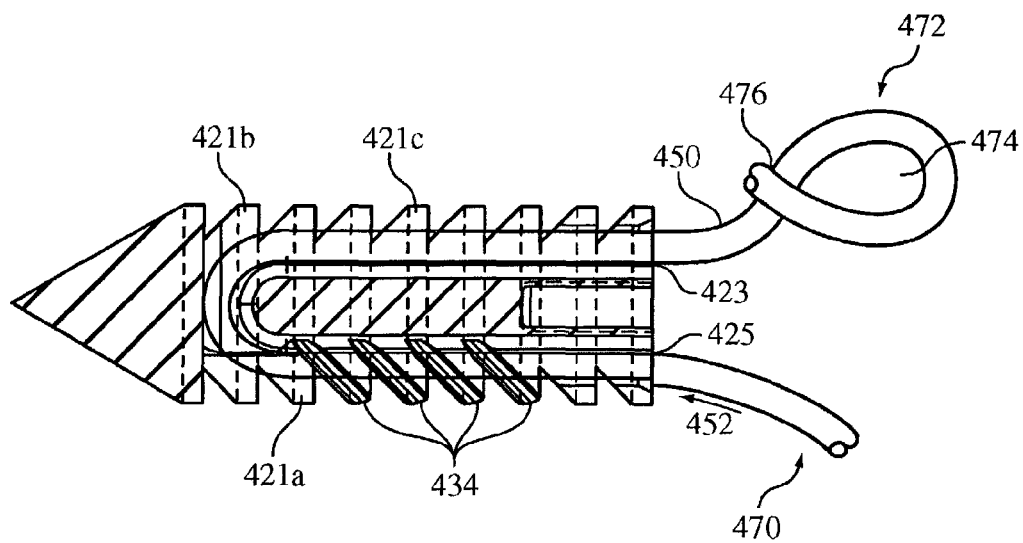

Referring to FIG. 10A, anchor 401' includes suture 450. Suture 450 has ends 470 and 472. Suture 450 also includes a loop 474, which is adjustable in diameter via a sliding attachment 476, at end 472 of suture 450. Referring to FIG. 10B, suture 450 is preferentially preloaded into opening 423, channel 421, and opening 425 of anchor 401'. As described above, suture 450 moves freely when traveling in a direction opposite that indicated by arrow 452. That is, when an doctor pulls end 470 of suture 450, suture 450 travels freely, entering through opening 423, traveling through channel portion 401c, through channel portion 421b, through channel 421a and ridges 434, and exiting through opening 425. When a doctor pulls end 472 (e.g., using loop 474), this causes suture 450 to travel in a direction indicated by arrow 452 and ridges 434 eventually restrict and prevent further motion in this direction as described above.

Figure 11:
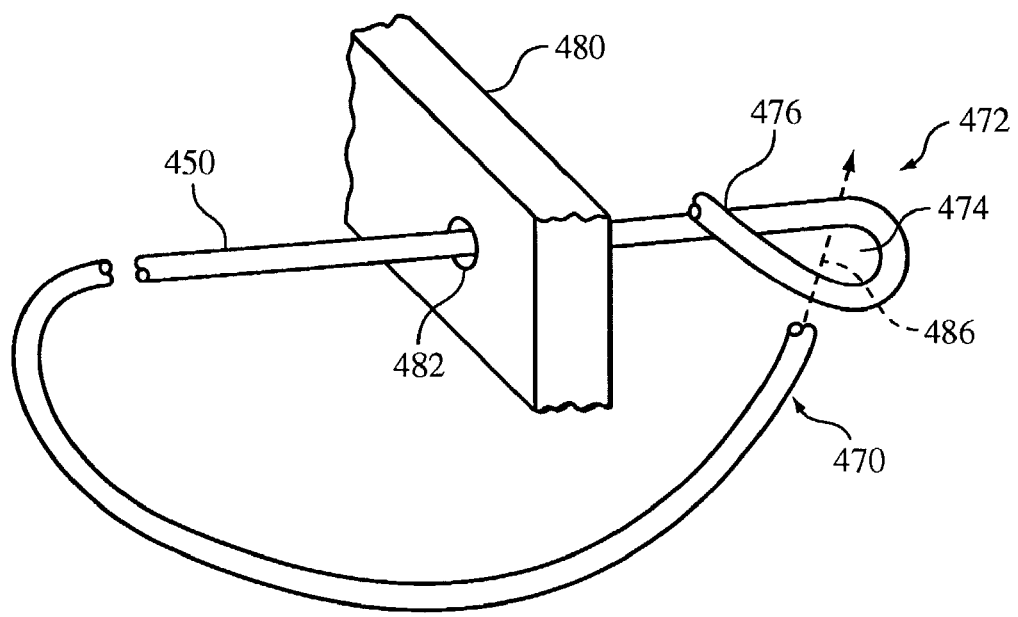
FIG. 11 illustrates attachment of a flexible member to candidate tissue.
Figure 12:
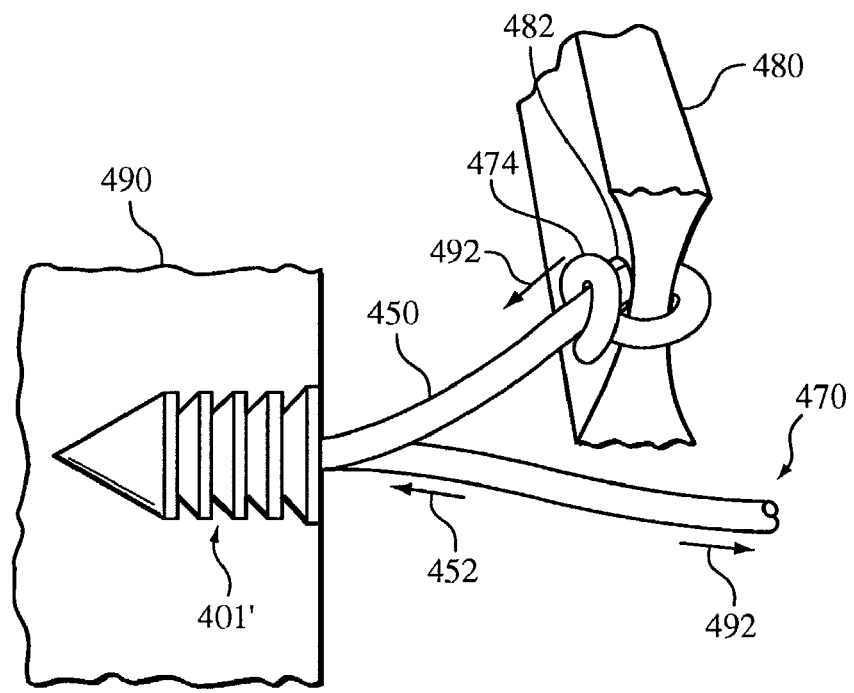
FIG. 12 illustrates an anchor in use.

FIG. 11 illustrates an example technique of attaching suture 450 to candidate tissue 480. Anchor 401' used in combination with suture 450 that has loop 474 enables the doctor to attach candidate tissue (e.g., tendon, ligament, cartilage and/or the like) to base tissue (e.g., bone and the like) without the use of knots. The doctor drills a hole 482 in candidate tissue 480. The doctor passes suture 450 through hole 482. The doctor passes end 470 of suture 450 through loop 474, as indicated by arrow 486. If the doctor had previously passed the suture 450 through anchor 401', then the doctor also passes anchor 401' through loop 474. The length of suture 450 is arbitrary. This enables the doctor to pass suture 450, and anchor 401' if attached, through loop 474 outside of the patient's body.

Referring to FIG. 11, the doctor inserts anchor 401' into base tissue 490. The doctor can insert anchor 401' using an insertion instrument having features that mate with insertion feature 432 of anchor 401'. Typically, the doctor drills a hole in base tissue 490 and inserts anchor 401' into the drilled hole. With anchor 401' inserted in base tissue 490 and candidate tissue 480 attached to suture 450 as described above, the doctor pulls suture 450, using end 470, in a direction indicated by arrows 492. As shown, this direction is opposite of the restricted direction indicated by arrow 452. (The illustrated directions are with respect to movement of suture through channel 421). Because this direction (i.e., indicated by arrow 492) is the unrestricted direction of channel 421, suture 450 moves freely and candidate tissue 480 moves towards base tissue 490. If candidate tissue 480 tries to pull away from base tissue 490, causing suture 450 to move in the direction of arrow 452, channel 421 restricts and prevents motion in this direction (i.e., indicated by arrow 452). This enables he doctor to locate candidate tissue 480 at a desired position and set the tension in suture 450 to a desired tension. When the doctor has positioned candidate tissue 480 at a desired location, the doctor can cut off any excess suture.

Additionally, instead of cutting off excess suture, the doctor can insert and use a series of anchors 401. The doctor passes suture 450 through subsequent anchors 401 after implantation of the first anchor and desired tensioning of the suture through the first anchor as described above. The doctor can tension/secure suture 450 as anchor placement progresses such that between any two anchors, the doctor sets the appropriate tension to effectively hold the tissue in place. See for example the descriptions associated with FIGS. 1 and 6 above.

Manufacture of anchor 401 can be done using a number of processes including machining and molding from biocompatible metal(s) and/or non-absorbable or absorbable polymer(s). Manufacture of the suture could be done using a number of processes and materials but the suture would preferentially be a braided fiber construction of non-absorbable or absorbable polymer(s).

A number of embodiments of the invention have been described. Nevertheless, it will be understood that various modifications may be made without departing from the spirit and scope of the invention. For example, a doctor can perform the steps described above for FIGS. 10 and 11 in a different order. Also, although the procedure of FIGS. 10 and 11 is referred to as a knotless procedure, a knot can be employed to create loop 474 (e.g., for sliding attachment 476). Also, a doctor can guide anchor 401 to the repair site through a cannula.

In other examples, the suture can be fixed to a first anchor and coupled to a second anchor configured to selectively restrict movement of the suture, as described above. A bone anchor can include only one or more than two cleats. The suture can couple more than two bone anchors in a tissue repair system. Any of a number of different geometries and/or types of bone anchor mechanisms as described in, e.g., U.S. Pat. No. 5,224,946 to Hayhurst et al., U.S. Pat. No. 5,236,455 to Hayhurst et al., and U.S. Pat. No. 5,100,417 to Cerier et al., the contents of all of which are incorporated herein by reference in their entirety, can be modified to include means according to the invention for selectively restricting passage of suture. Winding posts, side posts, holes, and openings can be replaced by any of a number of different structures that contact the suture and retain it in the bone anchor, including eyelets, bosses, etc. Edges can be formed by ridges protruding from the side walls.

Accordingly, these alternatives and others not described are within the scope of the following claims.

What is claimed is:

1. A bone anchor comprising:
    an anchor body having an outwardly extending, bone engaging formation configured to retain the anchor body within bone, the anchor body defining a path for passage of a member through the anchor body, the anchor body including a restrictor defining an opening having a first portion for permitting passage of the member therethrough, and a second portion for restricting passage of the member therethrough, the second portion including first and second surfaces between which the member is receivable, the first and the second surfaces for restricting passage of the member therethrough by compressing the member between the first and the second surfaces,
    the restrictor being configured such that movement of the member from the first portion to the second portion to restrict passage of the member through the restrictor is not along the path through the anchor body that the member takes to pass through the anchor body.

2. The bone anchor of claim 1, wherein the restrictor comprises a unidirectional mechanism configured to allow movement of the flexible member in a first direction when an end region of the flexible member is pulled and to restrict movement of the flexible member in a second direction when an opposite end region of the flexible member is pulled.

3. The bone anchor of claim 2, wherein the unidirectional mechanism further comprises:
    a portion including a transverse cross section having a tapered diameter, the tapered transverse cross section being in a plane substantially perpendicular to a direction of passage of the flexible member; and
    ridges disposed adjacent the portion, the ridges configured to direct the flexible member towards a widest portion of the tapered diameter of the portion when the flexible member travels in the first direction and towards a narrowest portion of the tapered diameter of the portion when the flexible member travels in the second direction.

4. The bone anchor of claim 1 wherein the restrictor includes an edge lining a wall of the opening.

5. The bone anchor of claim 4 wherein the edge is oriented obliquely to a direction of passage of the member through the opening.

6. The bone anchor of claim 5 wherein the restrictor includes multiple edges lining the wall of the opening.

7. The bone anchor of claim 6 wherein at least some of the edges are oriented at the same oblique angle relative to a direction of passage of the member through the opening.

8. The bone anchor of claim 6 wherein at least some of the edges are oriented parallel to each other.

9. The bone anchor of claim 6 wherein the edges are located in the first and second portion.

10. The bone anchor of claim 1 wherein a dimension of the second portion is narrower than a diameter of the member.

11. The bone anchor of claim 1 configured such that the member is movable between the first and second portions substantially perpendicularly to a direction of passage of the member through the opening.

12. The bone anchor of claim 1 wherein the anchor body includes a tissue penetrating tip.

13. The bone anchor of claim 1 wherein the anchor body includes a central body member.

14. The bone anchor of claim 13 wherein the central body member includes a driver coupling.

15. The bone anchor of claim 1 wherein the anchor body includes a resilient member for engaging bone tissue.

16. The bone anchor of claim 15 wherein the resilient member has a sharp, proximal edge for penetrating bone tissue.

17. The bone anchor of claim 1 wherein the anchor body includes multiple resilient members.

18. The bone anchor of claim 1 wherein the anchor body comprises a unitary body and a resilient member for engaging bone tissue, the resilient member having a sharp, proximal edge for penetrating bone tissue.

19. The bone anchor of claim 1 wherein the restrictor is configured such that moving the member along the path in a first direction causes the member to be moved from the first portion to the second portion.

20. The bone anchor of claim 19 wherein the restrictor is configured such that moving the member along the path in a second direction opposite the first direction causes the member to be moved from the second portion to the first portion.

21. The bone anchor of claim 1 wherein the second portion is proximal to the first portion.

22. The bone anchor of claim 1 wherein the restrictor is configured such that when the member is within the second portion the member is restricted from moving along the path in a first direction.

23. The bone anchor of claim 22 wherein the restrictor is configured such that the member is moved from the second portion to the first portion when the member is moved along the path in a second direction opposite the first direction.

24. The bone anchor of claim 23 wherein the restrictor is configured such that when the member is within the first portion, passage of the member along the path in the second direction is permitted.

25. The bone anchor of claim 1 wherein the restrictor is configured such that movement of the member along the path in a first direction acts to restrict passage of the member along the path, and movement of the member along the path in a second direction acts to permit passage of the member along the path.

26. The bone anchor of claim 1, wherein the restrictor defines the opening such that the first portion of the opening is different from the second portion of the opening.

27. The bone anchor of claim 26, wherein the restrictor defines the opening such that a narrowest width of the first portion is broader than a broadest width of the second portion.

28. The bone anchor of claim 27, wherein the opening is triangular in shape.

29. A tissue repair system comprising:
    a first bone anchor including a first anchor body configured to be retained within bone, a second bone anchor including a second anchor body configured to be retained within bone, and a flexible member coupling the first and second bone anchors, at least one of the first and second anchor bodies includes a restrictor having first and second walls defining an opening therebetween for passage of a member therethrough and between which the member can be compressed, at least one of the walls having an edge oriented such that upon movement of the member through the opening between the walls in a first direction, the member is also repositioned within the opening by movement non-parallel to the first direction, the first and the second walls restricting passage of the member therethrough by compressing the member between the first and the second walls.

30. A bone anchor, comprising:

an anchor body having an outwardly extending, bone engaging formation configured to retain the anchor body within bone, the anchor body including a restrictor having first and second walls defining an opening therebetween for passage of a member therethrough and between which the member can be compressed, at least one of the walls having an edge oriented such that upon movement of the member through the opening between the walls in a first direction, the member is also repositioned within the opening by movement non-parallel to the first direction, the first and the second walls for restricting passage of the member therethrough by compressing the member between the first and the second walls.

31. The bone anchor of claim 30 wherein the edge is oriented such that upon movement of the member through the opening in a second direction opposite the first direction, the member is also moved not along the path.

32. The bone anchor of claim 30 wherein the restrictor includes a second edge lining the wall of the opening.

33. The bone anchor of claim 30, wherein the restrictor has a first portion permitting passage of the member through the restrictor, and a second portion restricting passage of the member through the restrictor, the restrictor being configured such that when tension is applied at least predominantly to a first end of the member, the member moves through the first portion of the restrictor, and the restrictor being capable of moving the member from the first portion to the second portion not along a path that the member takes through the restrictor when tension is applied to only a second end of the member.

34. A bone anchor comprising:

an anchor body having an outwardly extending, bone engaging formation configured to retain the anchor body within bone, the anchor body defining a path for passage of a member through the anchor body, the anchor body including a restrictor defining an opening having a first portion for permitting passage of the member therethrough, and a second portion for restricting passage of the member therethrough, wherein the opening is triangular in shape and the second portion includes first and second surfaces for restricting passage of the member therethrough by compressing the member between the first and the second surfaces, the restrictor being configured such that movement of the member between the first and second portions is not in a direction of passage of the member along the path through the anchor body.

35. A bone anchor comprising:

an anchor body having an outwardly extending, bone engaging formation configured to retain the anchor body within bone, the anchor body defining a path for passage of a member through the anchor body, the anchor body including a restrictor defining an opening having a first portion for permitting passage of the member therethrough, and a second portion for restricting passage of the member therethrough, the second portion including first and second surfaces between which the member is receivable to compress the member, the second portion for restricting passage of the member therethrough by compressing the member between the first and the second surfaces, the restrictor being configured such that movement of the member between the first and second portions is not in a direction of passage of the member along the path through the anchor body, the bone anchor being configured such that the member is movable between the first and second portions substantially perpendicularly to a direction of passage of the member through the opening.

36. A bone anchor comprising:

an anchor body configured to be retained within bone, the anchor body including a tissue penetrating tip, the anchor body defining a path for passage of a member through the anchor body, the anchor body including a restrictor defining an opening having a first portion for permitting passage of the member therethrough, and a second portion for restricting passage of the member therethrough, the second portion including first and second surfaces between which the member is receivable to compress the member, the second portion for restricting passage of the member therethrough by compressing the member between the first and the second surfaces, the restrictor being configured such that movement of the member from the first portion to the second portion to restrict passage of the member through the restrictor is not along the path through the anchor body that the member takes to pass through the anchor body.

37. A bone anchor comprising:

an anchor body configured to be retained within bone, the anchor body including a central body member, the anchor body defining a path for passage of a member through the anchor body, the anchor body including a restrictor defining an opening having a first portion for permitting passage of the member therethrough, and a second portion for restricting passage of the member therethrough, the second portion including first and second surfaces between which the member is receivable to compress the member, the second portion for restricting passage of the member therethrough by compressing the member between the first and the second surfaces, the restrictor being configured such that movement of the member from the first portion to the second portion to restrict passage of the member through the restrictor is not along the path through the anchor body that the member takes to pass through the anchor body.

38. A bone anchor comprising:

an anchor body configured to be retained within bone, the anchor body defining a path for passage of a member through the anchor body, the anchor body including a restrictor defining an opening having a first portion for permitting passage of the member therethrough, and a second portion for restricting passage of the member therethrough, the second portion including first and second surfaces between which the member is receivable to compress the member the second portion for restricting passage of the member therethrough by compressing the member between the first and the second surfaces, the restrictor being configured such that movement of the member between the first and second portions is not in a direction of passage of the member along the path through the anchor body, wherein the anchor body includes a resilient member for engaging bone tissue.

39. The bone anchor of claim 38 wherein the resilient member has a sharp, proximal edge for penetrating bone tissue.

40. The bone anchor of claim 38 wherein the anchor body includes multiple resilient members.

41. A bone anchor comprising:

an anchor body configured to be retained within bone, the anchor body defining a path for passage of a member through the anchor body, the anchor body including a restrictor defining an opening having a first portion for permitting passage of the member therethrough, and a second portion for restricting passage of the member therethrough, the second portion including first and second surfaces between which the member is receivable to compress the member, the second portion for restricting passage of the member therethrough by compressing the member between the first and the second surfaces, the restrictor being configured such that movement of the member between the first and second portions is not in a direction of passage of the member along the path through the anchor body, wherein the anchor body comprises a unitary body and a resilient member for engaging bone tissue, the resilient member having a sharp, proximal edge for penetrating bone tissue.

42. A bone anchor comprising:

an anchor body configured to be retained within bone, the anchor body having a proximal end and a distal end, the distal end terminating in a tissue penetrating tip, the anchor body defining a path for passage of a member through the anchor body, the anchor body including a restrictor defining an opening having a first portion for permitting passage of the member therethrough, and a second portion for restricting passage of the member therethrough, the second portion including first and second surfaces between which the member is receivable to compress the member, the second portion for restricting passage of the member therethrough by compressing the member between the first and the second surfaces, the restrictor being configured such that movement of the member between the first and second portions is not in a direction of passage of the member along the path through the anchor body.

43. A bone anchor comprising:

an anchor body having an outwardly extending, bone engaging formation configured to retain the anchor body within bone, the anchor body defining a path for passage of a member through the anchor body, the anchor body including a restrictor defining an opening having a first portion for permitting passage of the member therethrough, and a second portion for restricting passage of the member therethrough, the second portion including first and second surfaces between which the member is receivable to compress the member, the second portion for restricting passage of the member therethrough by compressing the member between the first and the second surfaces, the restrictor being configured such that movement of the member between the first and second portions is not in a direction of passage of the member along the path through the anchor body, wherein the restrictor includes multiple edges spanning a majority of the first and second portions and configured to urge the member to move between the first and second portions.

44. A bone anchor comprising:

an anchor body configured to be retained within bone, the anchor body defining a path for passage of a member through the anchor body, the anchor body including a restrictor defining an opening having a first portion for permitting passage of the member therethrough, and a second portion for restricting passage of the member therethrough, the second portion including first and second surfaces for restricting passage of the member therethrough by compressing the member between the first and the second surfaces, the restrictor being configured such that movement of the member from the first portion to the second portion to restrict passage of the member through the restrictor is not along the path through the anchor body that the member takes to pass through the anchor body, wherein no portion of the opening permits unrestricted movement of the member through the opening in two opposite directions along the path through the anchor body that the member takes to pass through the anchor body without acting on the member to restrict movement of the member.

* * * * *

UNITED STATES PATENT AND TRADEMARK OFFICE
CERTIFICATE OF CORRECTION

| | | |
|---|---|---|
| PATENT NO. | : 7,867,251 B2 | Page 1 of 1 |
| APPLICATION NO. | : 10/305998 | |
| DATED | : January 11, 2011 | |
| INVENTOR(S) | : Dennis Colleran et al. | |

It is certified that error appears in the above-identified patent and that said Letters Patent is hereby corrected as shown below:

Column 3, Line 18, delete "FIGS." and insert -- FIG. --;

Column 6, Line 31, delete "228b ." and insert -- 228b. --;

Column 7, Line 9, delete "corticol" and insert -- cortical --; and

Column 15, Line 1, Claim 38, delete "member" and insert -- member, --.

Signed and Sealed this
Fifth Day of April, 2011

David J. Kappos
*Director of the United States Patent and Trademark Office*